United States Patent [19]

Molin et al.

[11] Patent Number: 4,806,471
[45] Date of Patent: Feb. 21, 1989

[54] PLASMIDS WITH CONDITIONAL UNCONTROLLED REPLICATION BEHAVIOR

[75] Inventors: Søren Molin, Holte, Denmark; Janice A. Light, Henley-on-Thames, United Kingdom; Jens E. L. Larsen, Jordløse, Denmark

[73] Assignee: A/S Alfred Benzon, Copenhagen, Denmark

[21] Appl. No.: 610,765

[22] Filed: May 16, 1984

[63] Continuation at PCT DK83/00084, Sept. 9, 1983, published as WO84/01171 on Mar. 29, 1984.

[51] Int. Cl.$^4$ ................... C12N 15/00; C12N 1/20; C12P 21/00; C12P 19/34
[52] U.S. Cl. ........................... 435/68; 435/70; 435/172.3; 435/517.1; 435/320; 435/252.33; 935/29; 935/32; 935/92; 536/27
[58] Field of Search ............... 435/317, 172.3, 91, 435/231, 68; 536/235; 935/27, 29, 32, 72

[56] References Cited

U.S. PATENT DOCUMENTS

| | | | |
|---|---|---|---|
| 4,487,235 | 1/1985 | Uhlin et al. | 435/231 |
| 4,495,282 | 1/1985 | Uhlin et al. | 435/231 |
| 4,499,189 | 2/1985 | Uhlin et al. | 435/253 |
| 4,631,257 | 12/1986 | Gelfand | 435/68 |

OTHER PUBLICATIONS

Sninsky et al. (1981) *Gene* vol. 16 pp. 275–286.
Cesareni et al. (1982 Oct.) *Proceedings National Academy Sciences, U.S.A.* vol. 79 pp. 6313–6317.
Erik et al. (1984) *Gene* vol. 28 pp. 45–54.
Uhlin et al. (1979) *Gene* vol. 5 pp. 91–106.
Rosen et al. (1981) *Nature* vol. 290, pp. 794–797.
Chamberlin MJ. (1976) in RNA Polymerase pp. 17–67 Colu Spring Harbor; Losik and Chamberlin eds.
Stougaard et al. (1981) *Proc. Nat'l Acad. Sci.* (U.S.A.) vol. 78 pp. 6008–6012.
Molin et al., Microbiology, 1981, pp. 408–411.
Rosen et al., Mol. Gen. Genet. 1979, 1980, pp. 527–537.
Light and Molin, Mol. Gen. Genet. 184, 1981, pp. 56–61.
Molin et al., Mol. Gen. Genet. 181, 1981, pp. 123–130.
Stougaard et al., the EMBO Journal 1, 1982, pp. 323–328.
Sussman and Jacob, Compt. Rend. Acad. Sci. 254, 1962, p. 1517.
Backman et al., Cell, Vol. 13(1), 1978, pp. 65–71.
WO, A1, 82/02901 (Cetus Corporation), 1982; EP, 0060045; JP, 57172000; AU, 82747/82.
Uhlin et al., Molec. Gen. Genet., vol. 165 (1978), pp. 167–179.
Nordstrom et al., Microbiology (1978), pp. 92–95.
Wong, Proc. Natl. Acad. Sci., vol. 79 (1982), pp. 3570–3574.
EP, A2, 0 013 830 (Cetus Corporation), 1980, and AU, 53922/79; JP 55104888.
Bittner et al., Chemical Abstracts, vol. 96 (1982), p. 63648v.
EP-A-0 003 (B. E. Uhlin).
EP-A-0 121 386 (Celltech Ltd.).
Scott, Microbiological review, vol. 48, 1984, pp. 1–23.

*Primary Examiner*—Thomas G. Wiseman
*Assistant Examiner*—S. Seidman
*Attorney, Agent, or Firm*—Bryan, Cave, McPheeters & McRoberts

[57] ABSTRACT

Plasmids useful as cloning vectors carrying an inserted regulatable promoter, transcription from the promoter regulating plasmid replication. Increased transcription leads to a substantially increased or uncontrolled plasmid copy number when host microorganisms containing the plasmid are cultivated under conditions securing such increased transcription. The regulatable promoter is preferably λ $P_R$, the activity of which is controlled by a temperature-sensitive λ cl repressor. To obtain gene products of the plasmids, host microorganisms to which such plasmids have been transformed are desirably cultivated at about 30° C. to secure a constant, low plasmid copy number during the seeding and multiplication stages of the microorganisms, after which the temperature is preferably shifted to about 36°–42° C. to obtain an uncontrolled plasmid copy number and an amplified amount of gene product.

65 Claims, 9 Drawing Sheets

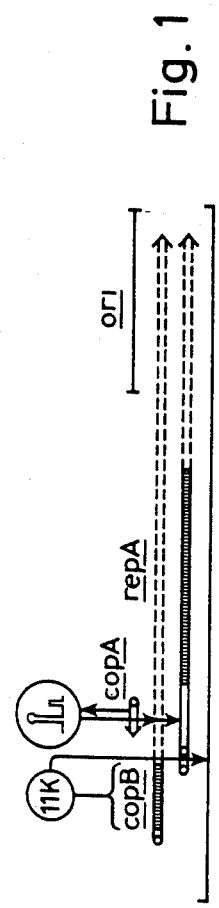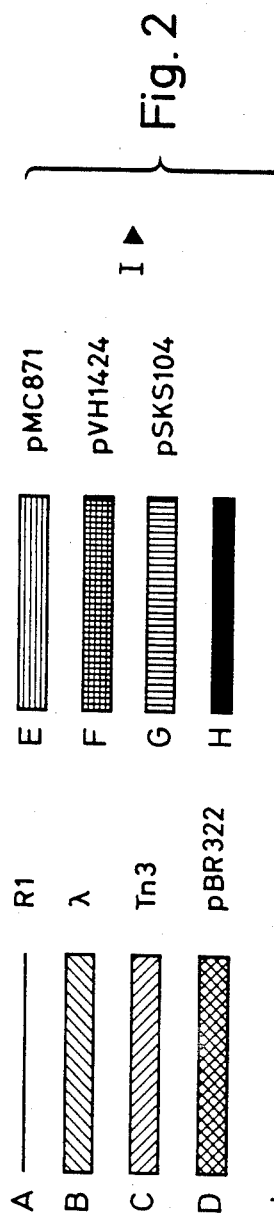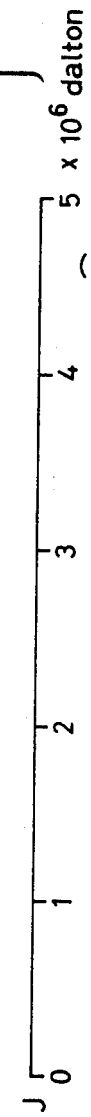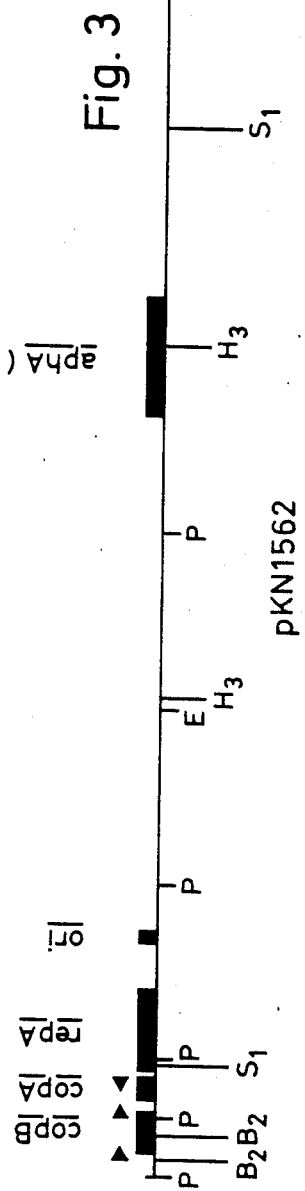

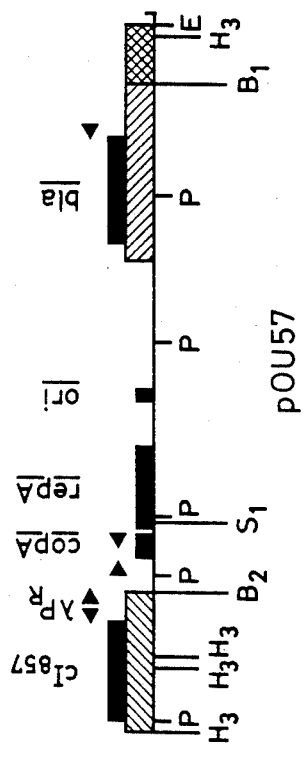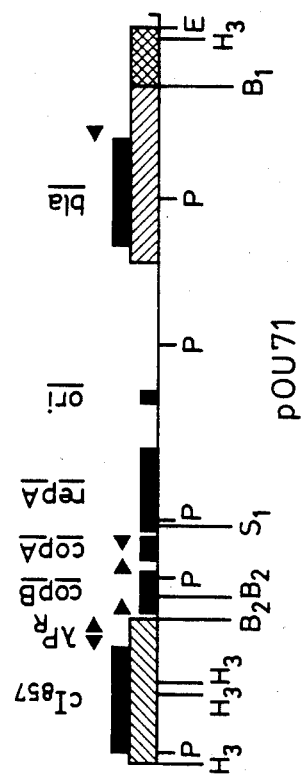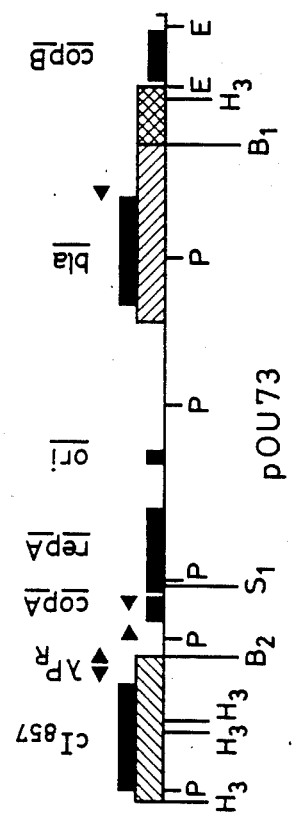

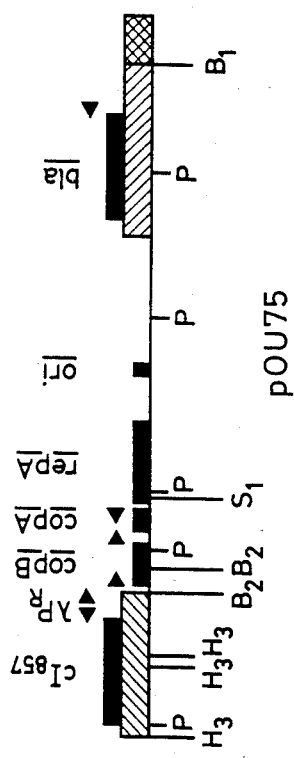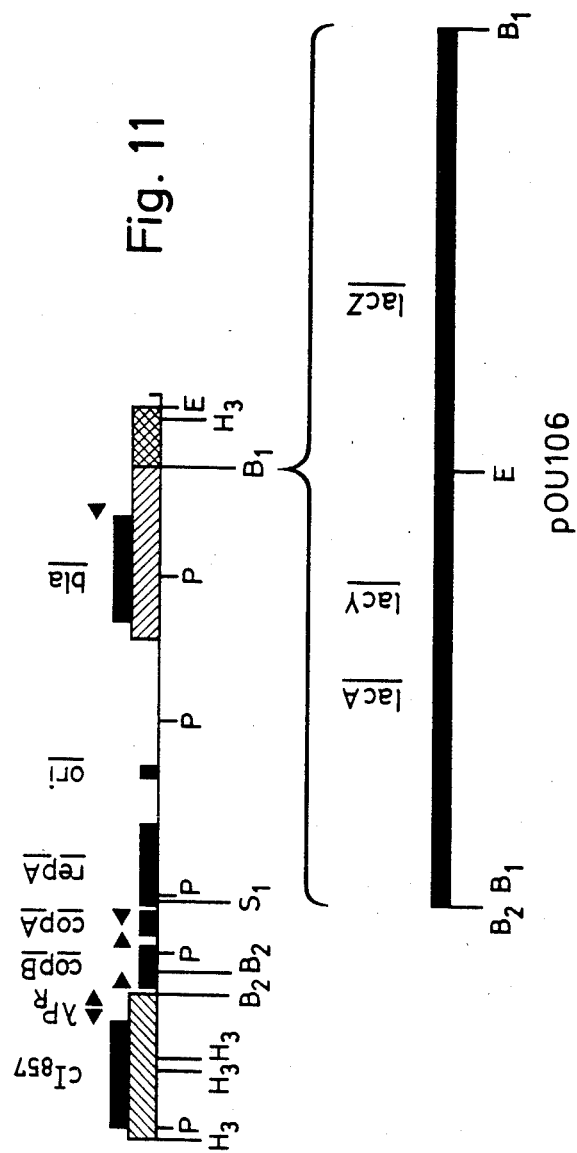
Fig. 10
Fig. 11

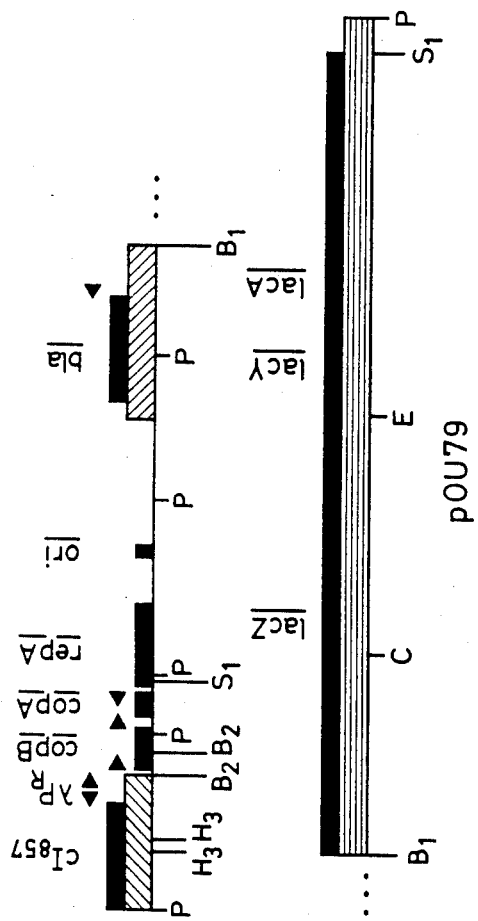
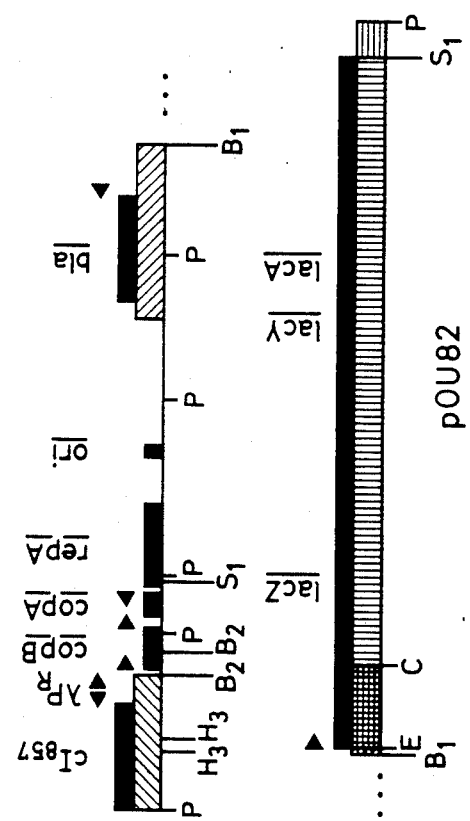

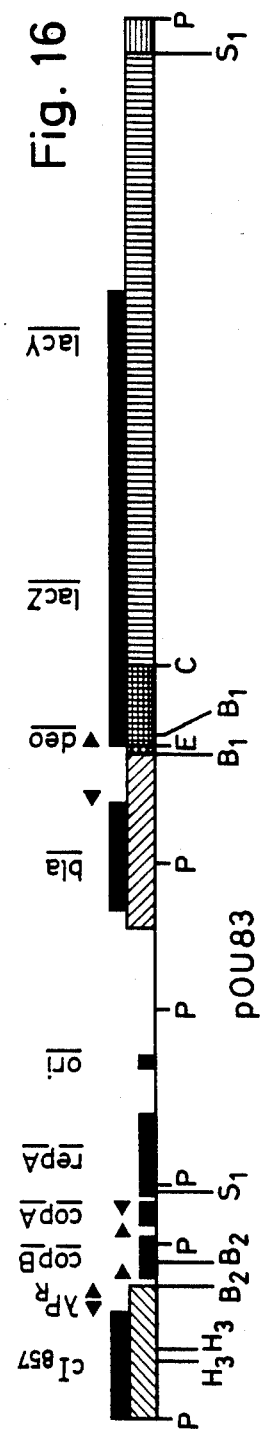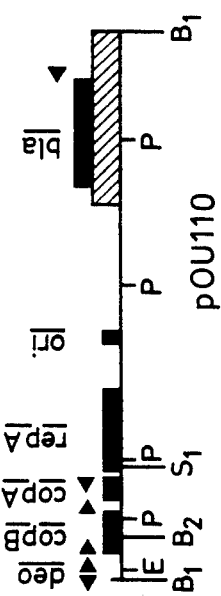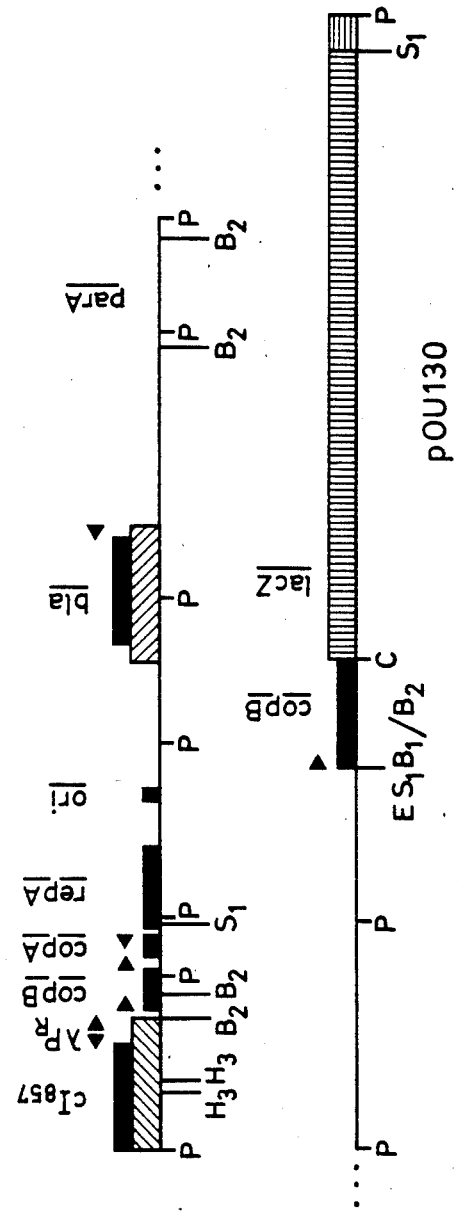

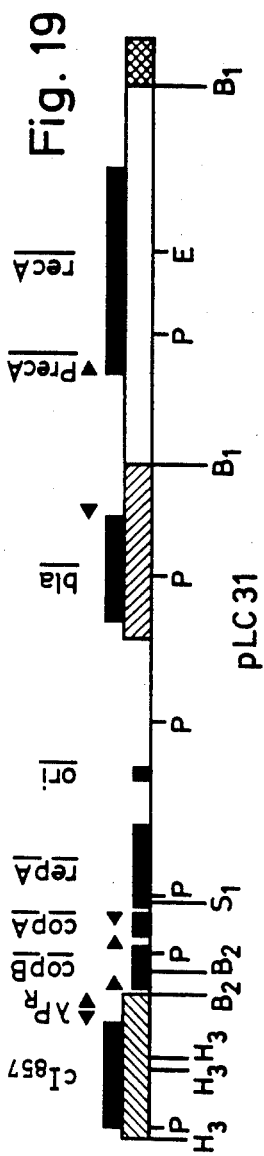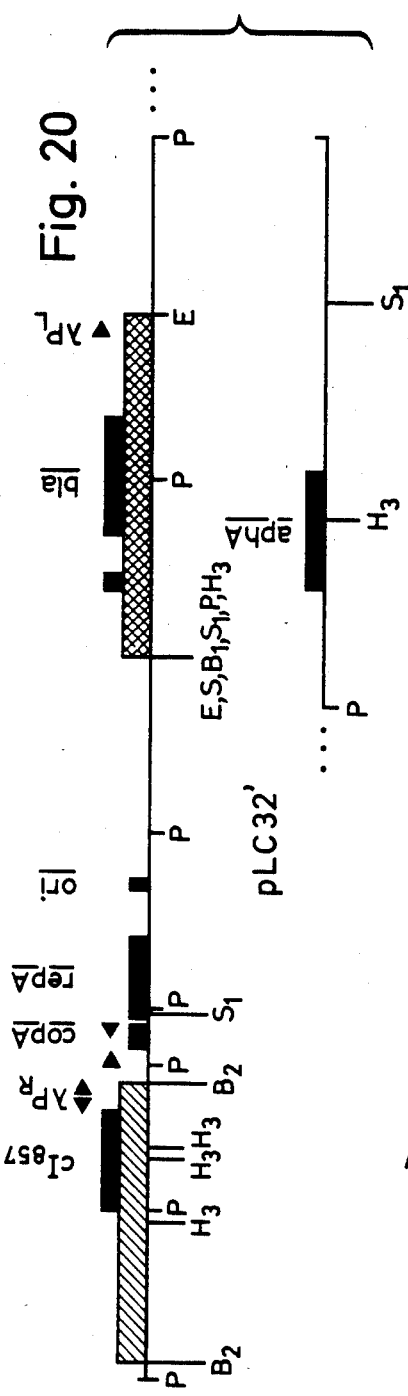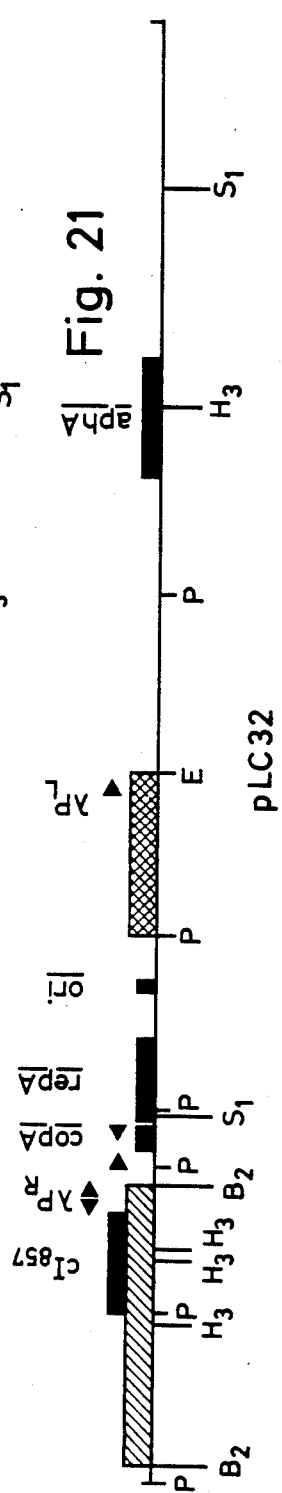

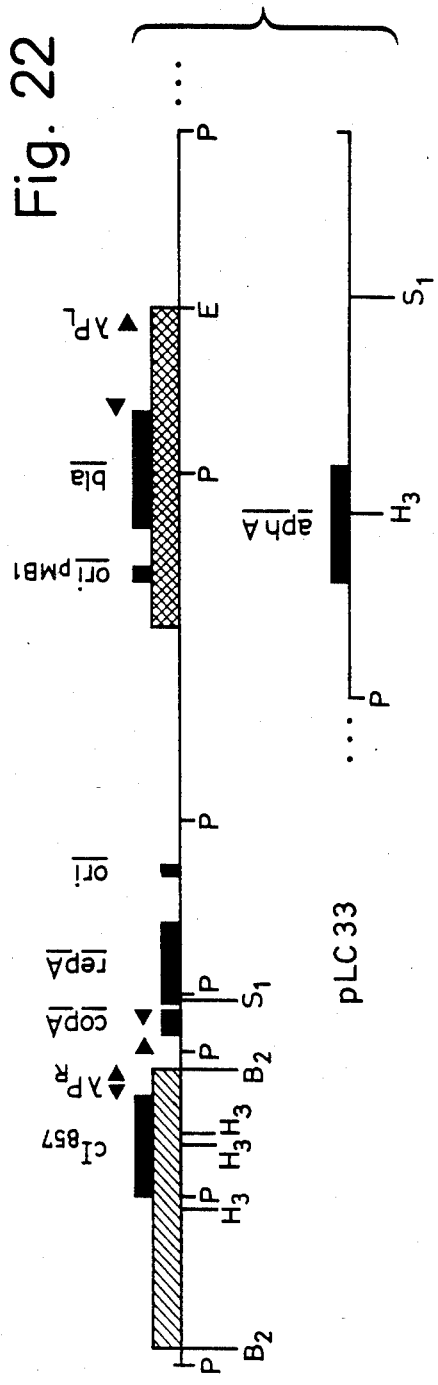
Fig. 22 pLC33
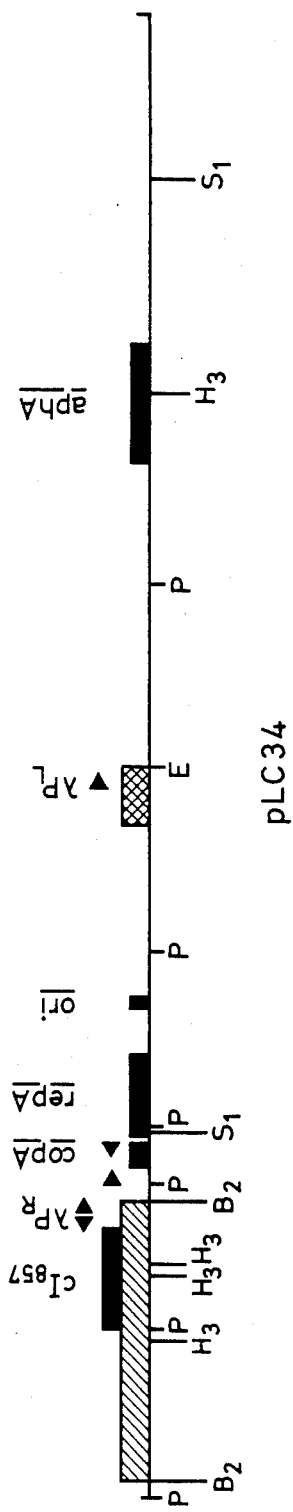
Fig. 23 pLC34

PLASMIDS WITH CONDITIONAL UNCONTROLLED REPLICATION BEHAVIOR

This application is a continuation of PCT/DK83/00084, filed Sept. 9, 1983, published as WO84/01171 on Mar. 29, 1984, which claims priority from Danish Ser. No. 4151/82, filed on Sept. 16, 1982, and Danish Ser. No. 4270/82, filed on Sept. 24, 1982.

BACKGROUND OF THE INVENTION

1. Field of the Invention

The present invention relates to novel plasmids useful as cloning and production vectors in the field of recombinant DNA technology, the replication behaviour of which is uncontrolled under conditions favourable therefor, and to a method for preparing such plasmids.

2. Description of the Related Art

Plasmids with conditional uncontrolled replication behaviour (so-called runaway plasmids) are known from, e.g., published European Patent Application No. 78101877.5. The replication of these plasmids is temperature-dependent in that the plasmids show a controlled, constant, low copy number when host bacteria carrying the plasmids are grown at one temperature, e.g. a temperature about 30° C., and an uncontrolled copy number when the host bacteria are grown at a different temperature, e.g. a temperature above about 36° C.

The plasmids disclosed in the above-mentioned patent application were isolated by chemical mutagenisation of plasmid R1, a wild-type plasmid which is known to replicate autonomously in *Escherichia coli*. The mutagenisation was performed in two stages, the first stage comprising the isolation of a plasmid-carrying bacterial clone in which the plasmid copy number was about 1–2 at 30° C. and 4–5 times higher at 40° C. and the second stage comprising the isolation of a bacterial clone in which the plasmid showed an uncontrolled copy number at the higher temperature. The plasmids showing runaway behaviour were thus double mutants of the parent plasmid.

The above-mentioned patent application also discloses miniplasmids which are useful as cloning vectors because they are relatively easily transformed to host bacteria due to their small size. These miniplasmids have retained the genes responsible for the temperature-dependent runaway replication behaviour.

As cloning and production vectors the plasmids disclosed in the above-mentioned patent application may be used to obtain gene products of inserted fragments of foreign DNA. The temperature-dependent replication of the plasmids may be utilized to produce amplified amounts of gene products from DNA fragments of, for instance, eucaryotic origin. Such amplification of gene product has not been available with conventional plasmid DNA amplification techniques which work by, for instance, the addition of chloramphenicol to the culture medium, as the presence of chloramphenicol causes the protein synthesis to stop.

The plasmids disclosed in the above-mentioned patent application may advantageously be used as cloning and production vectors in cases where an inserted foreign gene codes for a product which is detrimental to the bacterium to which the plasmids are transformed as, at low temperatures, the plasmids have a low copy number and, consequently, little gene expression. This means that during the multiplication stage of the culture which is conducted at low temperatures the bacteria are not likely to be impaired.

SUMMARY OF THE INVENTION

The present invention relates to novel plasmids which carry at least one regulatable promoter inserted in such a way that transcription therefrom regulates plasmid replication. In particular, the invention relates to plasmids in which the regulatable promoter causes substantially increased or uncontrolled replication when host microorganisms containing the plasmids are cultivated under conditions securing increased transcription from the promoter. The invention further relates to to a method for preparing such plasmids. The plasmids are useful as cloning and production vectors.

It is known to insert a regulatable promoter in order to control the expression of a structural gene inserted in the plasmid and coding for a desired gene product. It is, however, believed to be novel to insert a regulatable promoter in plasmids by means of which it is possible to regulate the number of plasmid copies formed.

A first aspect of the invention relates to a plasmid in which a regulatable promoter has been inserted in such a way that transcription from this promoter regulates replication, especially in such a way that increased transcription leads to a substantially increased or uncontrolled plasmid copy number. In the present specification and claims the term "regulatable promoter" refers to a promoter the activity of which, with respect to the rate of initiation of transcription, may be regulated by means of adjusting the conditions under which host microorganisms containing the promoter-carrying plasmids are grown. Such a regulatable promoter may, for instance, be a foreign promoter, i.e. a promotor not naturally related to the plasmid in which it is inserted. The promoter may be inherently regultable due to a particular DNA structure within the region of the promoter. An example of such a promoter is the one found in the known runaway plasmids (cf. the description below). Alternatively, the promoter may be controllable by means of a regulating factor which may either exert positive control, i.e. the plasmid does not attain uncontrolled replication unless the promoter is positively induced, e.g. by adding an inducing substance to the medium in which the host cells are grown, or the regulating factor may exert negative control. The latter type of controlling factor is also known as a repressor the activity of which may also be regulatable by means of adjusting the growth conditions of the host cells. The repressor gene may be located on the plasmid itself together with the promoter, on a separate plasmid in the same host microorganism or on the chromosome of the host microorganism. The repressor gene codes for a product which inhibits transcription from the inserted promoter so that replication is kept at a low, constant level. When, for some reason, the repressor becomes inactivated, no such control exists, and transcription increases.

Unless otherwise specified, the term "promoter", as used in the present specification and claims, is usually meant to include both a promoter whose activity inherently responds to changes in the growth conditions of the host cells and a promoter which is controlled by a regulating factor. The expression "a plasmid in which a regulatable promoter has been inserted" is also intended to apply to plasmids of the invention in which the promoter and the replicon regulated by the promoter have been inserted on the same DNA fragment, the promoter and the replicon being ultimately derived from different sources; this means that at one stage during the construction of the desired final plasmid, the promoter has been inserted into the plasmid from which the replicon is derived. The term "substantially increased or uncontrolled plasmid copy number" is understood to refer to the fact that when the conditions for growing the host microorganisms are altered to secure increased transcription from the promoter so that the plasmid loses its replication control, the plasmid copy number increases exponentially with a generation time of about 40–50%, or less, of that of the microbial populations. The increase continues until the host cell ceases to grow, usually after 4–5 cell doublings, or less, at which point the content of plasmid DNA in the cell is about 40–70% of the total amount of DNA, i.e. the plasmid copy number increases by a factor of about 25–1000 or even more. In other words, the plasmid copy number does not reach a steady state. This type of uncontrolled replication behaviour is also termed "runaway" behaviour.

The inventors' recently acquired knowledge of the replication control principle of R1-type plasmids is utilized in the construction of plasmids according to the invention (for a further explanation of this principle, see description of the preferred embodiments). When, in accordance with the principle of the invention, a regulatable promoter is inserted in the plasmid, increased transcription from the promoter leading to a substantially increased or uncontrolled plasmid copy number may be caused by, e.g. derepression of the promoter. This means that a repressor gene inserted together with the promoter and coding for a gene product which controls the promoter under certain conditions, becomes inactivated under different conditions so that transcription from the promoter is no longer inhibited, ultimately resulting in an uncontrolled plasmid copy number.

This is an important improvement compared to the known runaway plasmids which may, under varying conditions, exhibit differences in their replication properties. There are no indications that this is the case with the plasmids of the invention as the foreign promoter inserted will normally be one which is so strong (i.e. the frequency of initiation of transcription is high) that such changing conditions are without effect.

One of the conditions of cultivation by means of which it is possible to regulate the activity of the regulatable promoter is the temperature at which the host microorganisms are grown. The activity of the promoter may be temperature-dependent in itself, i.e. reacting to temperature changes during cultivation, or the regulating factor may be temperature-sensitive, e.g. a temperature-sensitive repressor.

The regulatable promoter may be a promoter from the bacteriophage λ which may be inserted as part of a DNA fragment which additionally carries the gene for a temperature-sensitive λ cI repressor controlling transcription from the promoter. The λ promoter may either by $\lambda P_R$ or $\lambda P_L$, especially $\lambda P_R$. However, other promoter systems inserted in the plasmids in accordance with the principles of the invention and influenced by other external factors than temperature may also be employed, such as promoters which are inducible with chemicals or regulatable by means of metabolites, such as lac, trp and deo promoters.

A favoured embodiment of the plasmid according to the invention is one in which the promoter regulatory system results in temperature-dependent replication behaviour of the plasmid. In particular, the temperature at which the plasmid shows a substantially increased or uncontrolled plasmid copy number is a temperature higher than the temperature at which the copy number is low. Plasmids according to the invention carrying a regulatable promoter the transcription pattern of which is temperature-dependent, for instance due to the presence of a temperature-sensitive repressor, show a constant, low copy number at one temperature, such as a temperature of about 30° C., because at this temperature the promoter is repressed and transcription from it is consequently kept at a low level, and a substantially increased or uncontrolled copy number at a higher temperature, such as a temperature in the range of about 36°–42° C., as the regulatory system becomes inactivated in this temperature range causing derepression of the promoter and, consequently, increased transcription from the promoter. It is preferred that runaway replication occurs at temperatures above about 39° C.

In the following description, reference will be made only to plasmids the replication of which is controlled by a regulatory system which is temperature-sensitive, especially by a temperature-sensitive repressor, although it will be understood that other types of conditions by means of which plasmid replication may be regulated may also be utilized in an analogous manner, as explained above.

One type of plasmid according to the invention is a plasmid in which a regulatable promoter has been inserted in place of part of one native replication regulatory gene of the plasmid. For the purposes of the present specification and claims, such a plasmid is designated a type A plasmid. When the plasmid is a derivative of plasmid R1, the regulator gene deleted from the plasmid is the copB gene, coding for one of the native replication inhibitors of the plasmid. The deletion of the copB gene results in a slight, stable increase in plasmid copy number. Thus, the plasmid has a copy number of about 20–40, preferably 20–30 and particularly 20–25 copies per cell at about 30° C. However, when the temperature is raised to about 40° C. the repressor function of the regulatable promoter is inactivated and replication becomes uncontrolled resulting in a plasmid copy number in the range of at least about 500–1000 copies per cell, dependent, inter alia, on the size of any foreign DNA fragment inserted in the plasmid (the larger the DNA fragment, the lower the number of plasmid copies formed), the effect of gene products of such foreign DNA and/or the microbial strain to which the plasmid is transformed. In some cases, however, the plasmid may form up to several thousand copies per cell at the higher temperature. At any rate, the content of plasmid DNA at the high temperature relative to the total DNA content is about 40–75%, usually 50–60%.

Another type of plasmid according to the invention is a plasmid with a copy number of about 3–5 copies per cell at one temperature, such as a temperature of about 30° C., and an uncontrolled copy number in the range of about at least 500–1000 copies per cell, dependent on the factors outlined above, and in some cases up to several thousand copies per cell, at a higher temperature, such as a temperature of about 42° C. Such a plasmid may be obtained by inserting the regultable promoter upstream of the native replication control gene(s) of the plasmid. For the purposes of the present specification and claims, such a plasmid is designated a type B plasmid. In the case of plasmid R1 derivatives, the regulatable promoter has been inserted upstream of both the copB and copA genes, so that both these native replication inhibitors have been retained which causes the plasmids to show the above-mentioned copy number pattern. However, if the plasmid is one that lacks the par region (the presence on the plasmid of the region responsible for partitioning has the effect that the plasmid is stably inherited; this effect is ascribable to one or more genes in the par region), the plasmid will be lost with a frequency of about 1% per generation at the low temperature because of the low copy number at the low temperature. Consequently, it may be advantageous to insert the par region into such a plasmid to ensure that the runaway replication of the plasmid will subsequently take place in all cells of the population.

The type B plasmid had the added advantage of a large copy number range. As the copy number at the low temperature is very low it is possible to insert foreign genes into the plasmids the products of which are partially toxic (lowering the growth rate) or even lethal to the microorganism to which the plasmid has been transformed. This is sometimes the case with products from eucaryotic genes, which are usually those of the highest interest to, e.g., the medical industry. Because of the low replication rate at the low temperature foreign genes are either not expressed at all or only in such small amounts that the cells are not damaged thereby and may be grown at the low temperature under normal conditions. This greatly enhances or facilitates the process of producing certain polypeptides which has hitherto not been possible at all, or only with great difficulty.

A third type of plasmid according to the invention is a plasmid with a copy number in the range of about 0.5–1 copy per cell (the figure 0.5 is understood to mean that the frequency of replication is less than one per cell cycle) at one temperature, such as a temperature about 30° C., and an uncontrolled copy number in the range of about at least 500–1000 copies per cell, dependent on the factors outlined above, and in some cases up to several thousand copies per cell, at a higher temperature, such as a temperature of about 42° C. Such a plasmid may be a plasmid carrying the regulatable promoter in the replication region from which part of one native replication regulatory gene has been deleted which has then been inserted outside the replication region, i.e. at a site where it is not naturally located. For the purpose of the present specification and claims, this plasmid is designated a type C plasmid. In the case of plasmid R1 derivatives from which the copB gene has been deleted, the copB gene is reinserted, not at its original site, but at the EcoRI site outside the replication region. Even so, the copB inhibitor protein influences the replication of the plasmid but in such a way that the plasmid shows the above-mentioned copy number pattern. However, if the plasmid is one that lacks the par region, the plasmid is lost with a frequency of about 5% per generation at the low temperature because of this extremely low copy number at the low temperature. Consequently, it would be even more advantageous with this plasmid than is the case with the type B plasmids to insert the par region into the plasmid to ensure that the runaway replication of the plasmid will subsequently take place in all cells of the population. The replication behaviour at the low and high temperatures, respectively, and hence the advantages of using this plasmid, is otherwise similar to that of the type B plasmids.

A second aspect of the invention pertains to a plasmid in which, in addition to the first regulatable promoter regulating transcription from the replication region, a second promoter has been inserted in a manner permitting the insertion of a structural gene the expression of which is controlled from the second promoter. This second promoter may be controllable, i.e. it may be possible to regulate its function by adjusting the conditions under which the host cell is grown by means similar to those of regulating the first regulatable promoter. A number of promoters are at present contemplated to be useful for this purpose, such as a lac promoter, trp promoter, deo promoter, recA promoter, $\lambda P_L$ promoter, etc. The $\lambda P_L$ promoter may prove to be especially advantageous as a second promoter controlling the expression of the structural gene as it is also regulated by the temperature-sensitive cI repressor, and therefore, amplification conditions are the same so that the cultivation of the host cells is simplified, and product amplification occurs simultaneously with the amplification of plasmid DNA. It should be noted that the second promoter may also be identical to the first regulatable promoter.

The second promoter may be inserted into type A, type B and type C plasmids. Such a plasmid has a constant, low copy number and very little or no gene expression at about 30° C., and a substantially increased or uncontrolled plasmid copy number, and gene expression, at a temperature in the range of about 36°–42° C. Preferably, the plasmid has an uncontrolled plasmid copy number and a very high gene expression at temperatures above 39° C.

The plasmids of the invention may be used as cloning and production vectors, i.e. plasmids which may be used in the field of recombinant DNA technology for the purpose of obtaining a wide variety of products for technical or medical purposes, particularly polypeptides and proteins or fragments thereof, enzymes and the non-proteinaceous products of reactions of enzymes with a compound in the nutrient medium, low molecular weight products such as hormones, and nucleic acids; products of eucaryotic, especially mammalian, genes are of particular interest. To be useful as a cloning and production vector it is advantageous, though not essential, for the plasmid to have, for at least one restriction endonuclease, a unique site cleavable by this endonuclease. The side should be one which, upon insertion of a fragment of foreign DNA, permits the resulting recombinant plasmid to replicate autonomously and which permits the regulatable promoter inserted in the plasmid to regulate the transcription of the replication region leading, when transcription from this promoter is increased, to a substantially increased or uncontrolled plasmid copy number. Restriction sites located within the replication region are thus not permissible as cloning sites, as this would cause the plasmid to lose its replication properties.

The plasmid of the invention is constructed by a method which comprises inserting a regulatable promoter into a plasmid in such a way that transcription from this promoter regulates replication and identifying the plasmid so treated by screening for those plasmids which show a substantially increased or uncontrolled plasmid copy number when transcription from the promoter is increased. When the regulatable promoter is $\lambda P_R$, it may be inserted by mixing plasmid and phage DNA, restricting with an appropriate endonuclease, heat inactivating and ligating the mixture, and transforming the ligation mixture to a microorganism.

The construction of such plasmids may be performed by inserting the promoter at random in different sites on the plasmid. By screening for plasmids with uncontrolled replication behaviour under conditions securing increased transcription from the regulatable promoter, the correct insertion is identified. A simple screening for such plasmids comprises analysing the growth properties of the plasmid-carrying cells at the various conditions. The amount of plasmid DNA in the host cells may be measured in different ways, notably by means of agarose gel electrophoresis in a manner known per se. This screening method is easily and speedily performed.

In a specific embodiment of the invention involving the construction of type A plasmids, the construction method comprises deleting part of one native regulatory gene and its promoter, in the case of the copB gene from plasmid R1 by cleaving with the restriction endonuclease BglII, and inserting a DNA fragment, such as a BglII fragment, including the regulatable promoter at this site.

In another embodiment of the invention involving the construction of type B plasmids, the construction method comprises inserting the regulatable promoter into the plasmid upstream of the native replication control system, in the case of plasmid R1 derivatives at the BglII site upstream of the copB gene by means of partial restriction with BglII, ligation and transformation to the microorganism in question, such as E. coli. Alternatively, the plasmid may be constructed by using the type A plasmid with the partially deleted native replication regulatory gene as a starting material and reinserting the native regulatory gene at its original site, in the case of R1-type plasmids by reinserting the copB gene at the BglII site.

A third embodiment of the invention, involving the construction of type C plasmids, comprises, by using the type A plasmids as a starting material, inserting one native regulatory gene in a region of the plasmid where it is not located in the wild-type parent, in the case of R1-type plasmids by inserting the copB gene as an EcoRI fragment at the EcoRI site outside the replication region of the plasmid by means of restriction with EcoRI, ligation and transformation.

A fourth embodiment of the invention comprises inserting, in addition to inserting the regulatable promoter, a second promoter at an appropriate restriction site permitting the insertion of a structural gene the expression of which is regulatable from the second promoter. As mentioned above, this site must not be located within the replication region of the plasmid.

The plasmids according to the invention are miniplasmids, i.e. they are appreciably smaller than their wild-type parent plasmids. Generally, they have a size in the range of about $2.5-15.0 \times 10^6$ daltons, often $2.5-10.0 \times 10^6$ daltons, usually $4.0-12.5 \times 10^6$ daltons, especially $4.0-5.0 \times 10^6$ daltons.

The uncontrolled replication behaviour of the known runaway plasmids appears to depend on the specific bacterial strain to which it is transformed, the culture medium in which the bacteria are grown and the DNA inserted. This dependence is probably due to the fact that the runaway replication behaviour of the known plasmids is, in part, caused by the substitution of a single nucleotide in the copB promoter causing a slight increase in the transcription rate which may be affected by environmental changes as regards the bacterial species and strain involved and/or the cultre medium as well as by foreign DNA inserted in the plasmids. The plasmids according to the invention do not seem to be similarly limited as the strong foreign promoter when activated/derepressed increases the transcription rate to such an extent that such changes are without significance. Consequently, these plasmids may be transformed to a wide variety of strains and they are also more reliable to handle than the known runaway plasmids.

The present invention also extends to plasmids derived from other wild-type plasmids than R1 and/or found in other plasmid-harbouring microorganisms than E. coli. It may also be envisaged to construct a plasmid of the above-described type which can be maintained in microorganisms not naturally harbouring plasmids. The replication system of several different microbial plasmids has been shown to be similar in many ways. For instance, all known plasmids require transcription if replication is to take place. By utilizing the principle of the invention it is possible to convey the uncontrolled replication phenotype to other plasmids so that plasmids already in use as cloning vectors and known to function well in a desired microorganism may acquire runaway behaviour. Thus, by inserting a regulatable promoter, e.g. $\lambda P_R$, at a proper position in such plasmids in such a way that transcription from this promoter regulates replication, uncontrolled replication will occur under conditions securing increased transcription from the promoter.

BRIEF DESCRIPTION OF THE DRAWING

Other objects and advantages of the invention will be apparent from the following description of preferred embodiments of the invention taken in connection with the accompanying drawing in which:

FIG. 1 is a schematic view of the replication region of the wild-type plasmid R1, FIG. 2 is a key to the symbols used in the following figures, and FIGS. 3-23 show restriction maps of the plasmids described in the examples.

In FIG. 1, a schematic view of the basic replicon of plasmid R1 is shown in which the shaded areas denote the translated regions, the blank areas denote the transcripts and the dotted lines denote possible transcripts. Within the circle, the enlarged view of the hairpin loops is meant to illustrate the high degree of secondary structure of the CopA-RNA. Ori stands for origin of replication. The horizontally placed arrows denote the direction of transcription.

In FIG. 2, a key to the symbols used in the following figures is shown in which I denotes DNA from R1-type plasmids; II denotes DNA derived from the bacteriophage λ (ED λ4); III denotes DNA from the Tn3 transposon (from ED λTn3); IV denotes DNA from plasmid pBR322; V denotes DNA from plasmid pMC871; VI denotes DNA from plasmid pVH1424; VII denotes DNA from plasmid pSKS104; VIII denotes structural genes and important sites; IX denotes a promoter with an indication of the direction of transcription; and X denotes a scale of the dimensions of the plasmids. The blank area denotes DNA from plasmid pBEU14.

In FIGS. 3-23, linear restriction maps of the plasmids described in the examples are shown in which the genotypes of the R1-type plasmids depicted are indicated above the horizontal line. Thus copB represents a gene coding for a polypeptide which represses transcription from the repA promoter between the copB and copA genes; copA represents a gene coding for an RNA molecule that inhibits translation of RepA-mRNA; repA represents a gene coding for a protein required for plasmid R1 replication; ori denotes the vegetative origin of replication; aphA represents a gene encoding resistance to kanamycin; bla represents a gene encoding resistance to ampicillin; lacA, lacY, and lacZ represents the inserted lac operon, of which lacA codes for transacetylase, lacY codes for permease and lacZ codes for β-galactosidase; $cI_{857}$ represents a gene coding for a temperature-sensitive repressor of the $\lambda P_R$ promoter; tnpR and tnpA represent genes coding for Tn3 transposition functions; par represents the region responsible for plasmid partitioning; recA represents a gene coding for a recombination protein; and PrecA represents the recA promoter. Below the horizontal line, the sites for restriction enzymes are shown in which P denotes PstI; $B_2$ denotes BglII; $S_1$ denotes SalI; E denotes EcoRI; $H_3$ denotes HindIII; $B_1$ denoes BamHI; S denotes SmaI; $B_2B_1$ denotes a fusion of a BglII site and a BamHI site; and C denotes ClaI. In FIG. 11, the plasmid depicted is drawn on the same scale as the plasmids in the other figures, and the bracketed insertion represents the insert lac genes.

DESCRIPTION OF THE PREFERRED EMBODIMENTS

Figure 4:
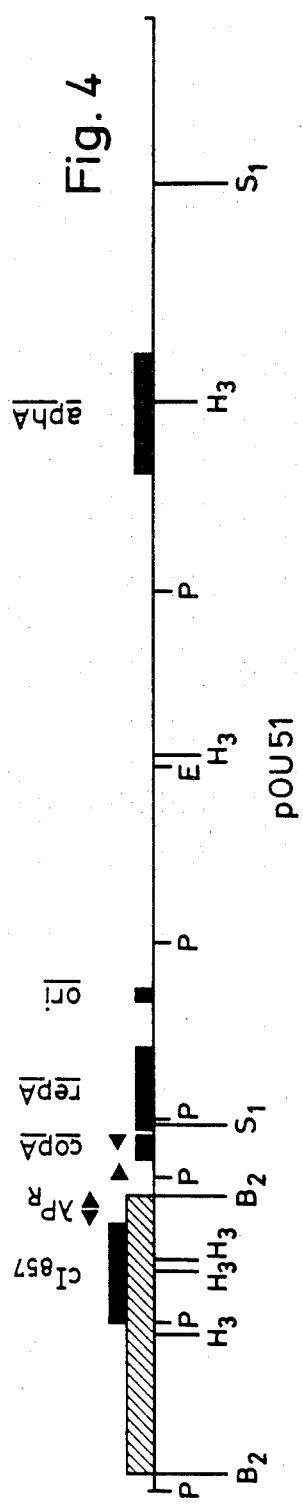

The Replication Control System of R1-type Plasmids

The Basic Replicon

Until recently, the replication control system of R1-type plasmids was not known. It has now been found that the genetic information needed for plasmid R1 replication and control of replication is carried in a 2500 base pairs long region consisting of three PstI fragments located within the resistance transfer factor (Molin et al., J. Bact. 138, 1979, 70–79).

This region is defined as the basic replicon and contains four important elements, three genes (copA, copB and repA) and the replication origin (Molin et al., Microbiology, 1981, 408–11). A physical genetic and functional map of the basic replicon is shown in FIG. 1. The gene repA codes for a function that is positively needed for replication. The gene product (according to the DNA sequence) is a protein of 278 amino acids and a molecular weight of about 33.000 daltons (Rosen et al., Mol. Gen. Genet. 179, 1980, 527-37). This protein has not been unambiguously identified, but the capacity to form protein from the repA gene has been clearly demonstrated by the use of translational gene fusions with the lacZ gene (Light & Molin, Mol. Gen. Genet. 184, 1981, 56–61). The biochemical function of the RepA protein has not yet been fully explored, but the RepA protein is believed to be a replication initiation factor.

The gene copA codes for a small (80–90 nucleotides long) unstable RNA molecule with a high degree of secondary structure (i.e. it forms haripin loops) (Stougaard et al., Proc. Natl. Acad. Sci. USA 78, 1981, 6008–6012). The CopA-RNA is an inhibitor of replication; mutations affecting the nucleotide sequence of the CopA-RNA may lead to an increased copy number (cop mutants). DNA-sequence analysis of copA mutants shows that all mutations are strikingly clustered in a loop area within 5 bases. These mutations result in a drastically reduced or total loss of inhibitor activity against the wild-type plasmid. Therefore, it may be concluded that the specificity of the inhibitor resides in the loop. It is also striking that in all copA mutants whose nucleotide sequence is known, a cytosine in the CopA-RNA has been replaced by a uracil (or, in one case, by an adenine). This strongly suggests that the CopA-RNA acts by nucleic acid/nucleic acid interaction. This conclusion is further strengthened by the fact that even those copA mutants that have lost all CopA activity against the wild-type plasmid retain some CopA activity against themselves. Moreover, the wild-type CopA-RNA most often has reduced inhibitory effect against copA mutant plasmids. Hence, a copA mutant is not only changed in the inhibitor, but also in the target, copT; a single base substitution thus leads to what phenotypically is a double mutant.

The copB gene codes for a basic protein of 86 amino acids with a molecular weight of 11.000 daltons. This protein is formed in substantial amounts. Deletion of the copB gene with its promoter leads to an eightfold increase in copy number; therefore, it is concluded that the copB protein acts as a replication inhibitor, i.e. as a negatively acting control element in the regulation of replication of plasmid R1 (Molin et al., Mol. Gen. Genet. 181, 1981, 123–30).

A double mutant (copAcopB) is unconditionally lethal to the host microorganism due to so-called runaway replication. Hence, the two control gene products act synergistically.

Transcriptional Activity in the Basic Replicon

There are three transcription initiation sites within the basic replicon, the copB promoter, the repA promoter (Light & Molin, Mol. Gen. Genet. 184, 1981, 56–61) and the promoter for the copA gene (Stougaard et al., op. cit.). The latter transcribes away from the origin region, whereas the two former transcribe towards the origin region. Consequently, both strands are transcribed in the copA region. The CopB transcript continues past the copB gene, and this transcript and the transcript that starts at the repA promoter both transcribe the repA gene.

Deletions of the copB gene constructed by restriction with BglII result in 8–10 fold increased copy number of plasmid R1. This is surprising since the copB gene promoter and the proximal part of the copB structural gene are deleted resulting (1) loss of copB activity and derepression of the repA promoter, and (2) loss of the contribution of the copB promoter to total repA expression so that the derepressed repA promoter effectively takes over total repA transcription from the copB promoter. The total effect should only be a twofold increase in the rate of transcription of the repA gene as the repA promoter has a strength that is two-fold increased above that of the copB promoter.

This apparent paradox is explained by the activity of the copA gene. The CopA-RNA is terminated in a normal termination structure with a stem ending in a series of U's. CopA-RNA control of the formulation of RepA protein depends on such proper termination. If transcription of the opposite strand is strong (convergent transcription), the efficiency of termination is decreased. Increased transcription from the repA promoter results in an extension of the CopA transcript to about 150–200 nucleotides. The extended CopA transcript does not function as a replication inhibitor, i.e., it is substantially inactivated, leading to an increased amount of RepA protein and eventually to an increased plasmid copy number (Stougaard et al., the EMBO Journal 1, 1982, 323–328).

Control of Replication

The products from two genes, copA and copB, negatively control replication of plasmid R1, i.e. they function as replication inhibitors. Through construction and analysis of repA-lac fusions it could be demonstrated that the two cop gene products act by negatively controlling the expression of the repA gene (Light & Molin, Mol. Gen. Genet. 184, 1981, 56–61). Therefore, plasmid R1 replication seems to be controlled by the regulation of the formation of a protein which is positively needed for, presumably, the initiation of replication of the plasmid.

By means of lac gene fusions it was also demonstrated that copA and copB products have separate targets. The target for the CopB protein is the repA promoter, where it acts by inhibiting initiation of transcription. However, the CopB protein is unable to interfere with transcription initiated upstream of the repA promoter. The CopA-RNA does not affect transcription but acts at a post-transcriptional level, i.e. by inhibiting translation of the RepA-mRNA.

Replication of the Runaway Mutants

The replication system of the plasmids disclosed in published European Patent Application No. 78.101877.5 is substantially the same as described above with respect to the wild-type R1 plasmids. Recent research by the present inventors has now partially established the cause for the existence of temperature-dependent plasmid mutants with runaway replication behaviour. As explained above, increased transcription towards the repA gene may lead to inactivation of the CopA-RNA molecule. In the runaway mutant plasmids disclosed in the above-mentioned patent application, the copB promoter is mutated by the substitution of a single nucleotide in a sequence, as shown:

(a) Wild-type plasmid: 5'- . . . TTCTCAAGT*C*GCT . . . -3'

(b) Runaway mutant: 5'- . . . TTCTCAAGT*T*GCT . . . -3'

The italics denote the nucleotide substitution. The region depicted is the RNA polymerase binding site.

This mutation was shown to cause increased transcription from the copB promoter, in particular at higher temperatures.

Replication of Plasmids Carrying a Regulatable Promoter

In the construction of the plasmids of the present invention, the inventors' recently acquired knowledge of the replication system of the wild-type R1 plasmids has been utilized. The replication of the plasmids of the present invention is not, however, made to rely on mutations in the plasmids as is the case with the runaway plasmids disclosed in published European Patent Application No. 78.101877.5. Instead, a foreign promoter has been inserted so that transcription of the replication region is at least partly controlled from this promoter. The promoter may be regulatable by adjustments in the conditions under which the host microorganisms are grown, and the regulation of promoter activity may be effected by various means, such as by altering the cultivation temperature or the composition of the growth medium.

When the regulatable promoter is one selected from a group of temperature-dependent promoters, it is preferably a promoter derived from bacteriophage λ, such as λ$P_R$ or λ$P_L$, in particular λ$P_R$. In phage λ, the $P_R$ promoter is controlled by the cI repressor which, in accordance with the principles of the invention, is derived from phage λ together with λ$P_R$ and inserted in a plasmid in the form of a BglII fragment (vide the appended plasmid maps, FIGS. 4–11). The wild-type cI repressor is not in itself temperature-sensitive, so in order to make the replication system regulatable by means of adjustments in the cultivation temperature, the specific cI repressor employed (cf. the following examples) is temperature-sensitive, coded by the mutant allele cI$_{857}$ (Sussman & Jacob, Compt. Rend. Acad. Sci. 254, 1962, 1517). The repressor is active, i.e. it represses the λ$P_R$ promoter, at low temperatures such as a temperature of about 30° C., whereas, at higher temperatures such as temperatures above about 39° C., it is denatured causing an inactivation of the repressor function and a derepression of λ$P_R$. As the inserted promoter is very strong, this results in drastically increased transcription towards repA which, in turn, leads to uncontrolled plasmid replication.

Alternatively, the regulation of the promoter may be effected by chemical means, i.e. by adjusting the composition of the medium in which the host microorganisms are grown, either by adding a chemical inducing the promoter, for instance by causing inactivation of the repressor controlling promoter activity and consequently derepression of the promoter or by securing the formation of a promoter-inducing metabolite leading to activation of the promoter. A specific example of a chemically inducible promoter is the deo promoter from *E. coli* which is subject to negative control by two chromosomal repressor proteins, the products of the deoR and cytR genes. The deo promoter may be depressed by adding cytidine to the growth medium, as cytidine acts by affinity to the repressor causing a conformational change thereof so that it ceases to function as a repressor. Additionally, positive control may be exerted on the expression from the deo promoter through the effect of catabolite repression. Activation of the crp (catabolite repressor protein) protein by cyclic AMP (cAMP) results in stimulation of the deo promoter activity; high cellular levels of cAMP are known to be correlated with low levels of glucose in, or the abence of glucose from, the growth medium, which may be obtained by adding only a limited amount of glucose to the medium, e.g. an amount of about 0.01%, together with another carbon source such as glycerol or succinate. When the glucose is consumed by the cell, the resulting increase in the intracellular level of cAMP will active the deo promoter leading to an increased replication rate of the plasmid carrying the promoter. Thus, if the deo promoter is inserted upstream of the copB gene in a plasmid R1 derivative, induction of the promoter leads to increased or completely uncontrolled replication. The uncontrolled replication behaviour may reversed by adding glucose to the growth medium so that the copy number of the plasmid slowly decreases to pre-induction level. Another example of a chemically regulatable promoter is the lac promoter which is induced by the presence of lactose in the nutrient medium leading to increased or uncontrolled replication. In this case, too, the process may be reversed by dosing the amount of lactose added to the medium so that it is eventually consumed by the cells.

Insertion in the proper position and orientation of a DNA fragment carrying a regulatable promoter in place of part of one native replication regulatory gene, e.g. in place of the BglII fragment covering part of the copB gene of plasmid R1, results in a plasmid derivative the replication rate of which is at least in part controlled by the inserted promoter (a type A plasmid).

Insertion in the proper orientation of a DNA fragment carrying a regulatable promoter immedately upstream of the native replication regulagory gene, in the case of plasmid R1 derivatives the copB gene, results in a plasmid with slightly different replication properties (a type B plasmid).

As mentioned above, type B plasmids which lack the par region are lost with a frequency of about 1% per generation. Without selection for the presence of the plasmids in a culture, the plasmid is eventually lost from cells grown at about 30° C. In order to stabilise the plasmid, it is possible to insert a DNA fragment carrying a par region from, for instance, a wild-type R1 plasmid in a type B plasmid which leads to complete stability (no loss) of the plasmid from cells grown under similar conditions. Plasmid stability may be determined by initially growing cells containing type B plasmids in which lac genes as well as the par region has been inserted and, as a control, cells containing type B plasmids carrying the lac genes, but not the par region, selectively on plates containing an antibotic (to which the plasmids mediate resistance) to ensure the presence of both kinds of plasmid in the starting colonies. Samples of both colonies are then streaked on plates not containing any antibiotic so that the cells are left to grow without selection for a number of generations (cell doublings) such as, for instance, 25 generations. Finally, cells from both the resulting colonies are streaked onto McConkey lactose indicator plates where the cells originally containig plasmids carrying the par region form red colonies which shows that the plasmids have been retained, whereas the control cells originally containing plasmids without the par region form both red and colourless colonies which means that during the selection-free period the plasmids have been lost from some of the cells. Thus, it is demonstrated that plasmids in which the par region has been inserted have become completely stable (cf. Example 11). This stabilising effect is especially important if an inserted DNA fragment causes a reduction of the growth rate of the plasmid-carrying cells compared to plasmid-free cells.

Finally, insertion of a DNA fragment carrying the native replication regulatory gene, such as the copB gene of plasmid R1, into a site outside the replication region of a type A plasmid results in a plasmid with particular replication properties (a type C plasmid).

The desirability of plasmid stability described above with respect to type B plasmids is even more pronounced where type C plasmids are concerned, since these, as mentioned above, have an even lower copy number at the low temperature and are therefore lost with a higher frequency than type B plasmids if they lack the par region. The type C plasmids may be similarly stabilised by inserting the par region in the plasmids in the case of plasmids where it is not already present.

According to a particular aspect of the invention, the plasmid carries, in addition to the first regulatable promoter, a second promoter located outside the replication region which promoter regulates the expression of an inserted foreign structural gene which, for instance, codes for a desired polypeptide. This additional promoter may, for instance, be the cI promoter located on the fragment additionally carrying the $\lambda P_R$ promoter and the cI gene, which cI promoter is controlled by the cI gene product and trascribes in the opposite direction of $\lambda P_R$. Downstream of the cI promoter it is possible to insert a structural gene the expression of which is regulatable by this promoter. As an example, lac genes (known as the lac operon) lacking the lac promoter have been inserted downstream of the cI gene and the gene product amplification obtained suggested that transcription of the lac genes was, at least in part, controlled by the cI promoter (cf. Example 8). It was thus demonstrated that it is possible to use the plasmids of the invention as cloning vectors for the insertion of a foreign gene. The cI promoter has the advantage of being regulatable by the cI repressor, too, so that amplification of the gene product takes place simultaneously with amplication of plasmid DNA.

The second promoter may also be a $\lambda$ promoter, such as $\lambda P_L$, or it may be recA promoter. When the second promoter is $\lambda P_L$, it may be inserted in the plasmid as a BamHI-BglII fragment from phage $\lambda$, thus producing a convenient cloning site (BamHI) for the insertion of DNA fragments generated by several restriction enzymes, such as BamHI, BglII, Sau3A and BclI. $\lambda P_L$ may also be inserted on an appropriate DNA fragment from a plasmid carrying the promoter. $\lambda P_L$ is advantageous as a second promoter because it is also controlled by the temperature-sensitive cI repressor so that amplification conditions are the same.

If, on the other hand, the promoter is recA, it may be inserted in the plasmid of the invention as a BamHI fragment from, e.g., pBEU14 (Uhlin and Clark, J. Bact. 148, 1981, 386–90). This promoter functions in different ways depending on the microbial strain to which the recA promoter-carring plasmid has been transformed. In a recA strain, recA is controlled by the lexA repressor, which is located on the chromosome of the microorganism. At, e.g., a temperature-induction of uncontrolled replication the copy number of the plasmid and hence the number of recA promoters gradually increases. As the lexA repressor is only produced in small amounts and functions by bindig tightly to the recA promoter region, the available amount of lexA repressor will gradually be titrated when the copy number increases. Thus, there is gradual derepression of recA and when the plasmid copy number becomes higher, the transcription from recA will correspondingly increase.

The Plasmids of the Invention as Cloning and Production Vectors

In their capacity as cloning and production vectors, the plasmids of the invention have a number of characteristic properties:

(1) The plasmids are small with a molecular weight of about $4.0-12.5 \times 10^6$ daltons. The small size facilitates handling and improves transformation efficiency.

(2) The plasmids have a number of unique sites for restriction endonucleases. The term "unique" is understood to mean that, for a specific restriction endonuclease, the plasmid has one and only one site cleavable by the enzyme.

As already mentioned, restriction sites located within the replication region are not permissible as cloning sites. Thus, in the plasmids described in the following examples, the restriction sites SalI and PstI are not suitable as cloning sites as they are located in the replicon of the plasmid, whereas the restriction sites EcoRI and BamHI are not located within this critical region and thus form useful sites for the introduction of foreign DNA. If a suitable restriction site is not to be found on the plasmid itself, it may be constructed by inserting a small DNA fragment (known as a linker) containing such a site ito the plasmid as described in Example 4.

In order to ensure the expression of the inserted structural gene, however, it is also necessary to have an appropriate translational start signal (ribosomal binding site) located upstream of the structural gene itself but downstream of the second promoter. One way of securing the presence of the ribosomal binding site is to insert a variety of of DNA fragments (e.g. as linkers), which may be prepared synthetically, each carrying the translation start signal for a different structural gene. Alternatively, a DNA fragment carrying a gene which is already known to be expressed in microorganisms may be inserted in the runaway cloning vectors in toto, thus ensuring the presence of the correct translation start signal.

(3) Although, as mentioned above, it is an advantage to have as small a cloning vector as possible, it is, for many purposes, practical that the cloning vector carries genes for the espression of a so-called marker useful for the identification and/or selection of cells carrying the plasmid. The most useful marker is antibiotic resistance, for example ampicillin resistance, as this permits, after a treatment for transforming a recombinant plasmid to a microbial host, an easy counter-selection of microorganisms which have not received the recombinant plasmid. Another marker which is present in all the plasmids described in the following examples is λ immunity which is encoded by the cI gene. A further useful property in plasmids of the invention may be the presence of a gene mediating a selectable phenotype within which a unique restriction site is located. Insertion of a DNA fragment at this site results in insertional inactivation of the gene. An example of this is described in Example 9 with respect to the gene mediating the Lac+ phenotype and Example 12 with respect to the gene encoding chloramphenicol resistance. When it is desired to introduce a marker, for instance antibiotic resistance, into a plasmid of the invention which is to be used as a cloning vector, this may be done by transposition or by inserting a foreign DNA fragment in a manner known per se. An example of such transposition is shown in Example 4.

Methods of cultivation

The present invention also provides a method for producing a gene product of plasmid DNA which comprises cultivating microorganisms carrying a plasmid in which a regulatable promoter has been inserted in such a way that transcription regulates replication, especially in such a way that increased transcription from this promoter leads to a substantially increased or uncontrolled plasmid copy number, the method comprising at least a period of cultivation under conditions securing increased transcription from the regulatable promoter resulting in a substantially increased or uncontrolled plasmid copy number, and harvesting, from the microbial culture, a gene product of the plasmid. The cultivation per se is suitably performed using conventional techniques, including conventional nutrient media which are known to be optimal to the microbial species in question. Also, the harvesting of the gene product is performed in accordance with well-known methods adapted to the identity and properties of the particular gene product prepared, the properties of the host microorganism, etc. The present invention further provides a method of growing the host microorganism to which the plasmid according to the invention has been transformed under conditions resulting in a constant, low plasmid copy number during the seeding and multiplication stages until the desired number of cells has been obtained and then cultivating the host microorganism under conditions leading to a substantially increased or uncontrolled plasmid copy number.

Thus, the cultivation may initially be performed under conditions where any transcription from the promoter does not significantly influence the copy number of the plasmid, after which a substance which induces promoter activity is added to the culture medium in an amount leading to substantially increased or uncontrolled replication. If desired, these cultivation conditions may be reversed after a period of time sufficient to obtain a substantial amplification of the plasmid, but sufficiently brief to avoid any substantial impairment of the microbial culture, the substance is removed from the culture medium leading to a slow decrease in plasmid copy number until it eventually reaches the pre-induction level. In this context, the term "removed" need not imply a complete absence of the substance in question from the culture medium, but only a reduction in the concentration of the substance to an extent where it no longer has any effect.

In an alternative method, employing a promoter which is inhibited, rather than induced, by a certain substance, the microbial culture may initially be cultivated in the presence of the substance inhibiting the activity of the particular promoter used, after which the concentration of the substance is reduced, e.g. by diluting the culture medium or by being gradually consumed by the cells, to an extent leading to activation of the promoter, thus causing a substantially increased or uncontrolled plasmid copy number. If desired, the cultivation conditions may be reversed after a period of time sufficient to obtain a substantial amplification of the plasmid, but sufficiently brief to avoid any substantial impairment of the microbial culture, by adding the substance inhibiting promoter activity in an amount leading to a slow decrease in plasmid copy number until it reaches the preinduction level.

The conditions under which the microorganism is grown may also comprise at least a period of cultivation at or near a temperature at which the plasmid copy number is substantially increased or uncontrolled.

If the regulatable promoter is temperature-dependent or regulated by a temperature-sensitive factor, it is preferred that the propagation of the microorganism transformed with a plasmid of the invention up to a production size culture is performed at or near the temperature at which the plasmid shows a constant, low copy number in order to avoid any inhibition of microbial growth by an increasing plasmid and gene product concentration. Then, the temperature may be shifted to a temperature at which the plasmid shows a substantially increased or uncontrolled copy number. After a suitable production period, often until the growth of the microorganism is inhibited by the production of plasmid DNA and/or gene products from the plasmid, the harvesting of the gene product is performed. Depending on the particular conditions, it may be desired to perform the production cultivation continuously at a temperature which only approaches the temperature at which the plasmid copy number is substantially increased or uncontrolled so as to permit the survival and continued growth of the host microorganism concomitantly with the formation of increased amounts of a gene product of the plasmid (which may then be continuously or intermittently harvested from the culture in a manner known per se).

Alternatively, the microorganism may be propagated up to a production size culture at the temperature at which the plasmid copy number is constant, whereupon the temperature is shifted to a temperature at or near the temperature at which the plasmid copy number is substantially increased or uncontrolled, and this temperature is maintained for a period of time sufficient to obtain a substantial amplification of the plasmid, but sufficiently brief to avoid any substantial impairment of the microbial culture, after which the temperature is once more shifted to a temperature securing a low, constant plasmid copy number, and a production cultivation is continued at this latter temperature causing a slow decrease in plasmid copy number until it reaches its initial level. This cultivation method is particularly important when the foreign gene inserted in the plasmid is derived from an organism which is not viable at temperatures above about 30° so that gene products of such a gene may be denatured at higher temperatures. Moreover, the yield of gene product is usually higher when this method of cultivation is employed (cf. Example 16; compare Uhlin et al., Gene 6, 1979, 91–106, Table II).

The temperature at which the plasmid copy number is substantially increased or uncontrolled may be higher than the temperature at which the plasmid has a constant, low copy number. This higher temperature may for instance be a temperature in the range of about 36°–42° C.

DESCRIPTION OF THE DRAWINGS

Reference is made to the drawing in which

FIG. 1 is a schematic view of the replication region of the wild-type plasmid R1, FIG. 2 is a key to the symbols used in the following figures, and FIGS. 3–14 show restriction maps of the plasmids described in the examples.

In FIG. 1, a schematic view of the basic replicon of plasmid R1 is shown in which the shaded areas denote the translated regions, the blank areas denote the transcripts and the dotted lines denote possible transcripts. Within the circle, the enlarged view of the hairpin loops is meant to illustrate the high degree of secondary structure of the CopA-RNA. Ori stands for origin of replication. The horizontally placed arrows denote the direction of transcription.

In FIG. 2, a key to the symbols used in the following figures is shown in which A denotes DNA from R1-type plasmids; B denotes DNA derived from the bacteriophage λ (EDλ4); C denotes DNA from the Tn3 transposon (from EDλTn3); D denotes DNA from plasmid pBR322; E denotes DNA from plasmid pMC871; F denotes DNA from plasmid pVH1424; G denotes DNA from plasmid pSKS104; H denotes structural genes and important sites; I denotes a promoter with an indication of the direction of transcription; and J denotes a scale of the dimensions of the plasmids. The blank area denotes DNA from plasmid pBEU14.

In FIGS. 3–14, linear restriction maps of the plasmids described in the examples are shown in which the genotypes of the R1-type plasmids depicted are indicated above the horizontal line. Thus, copB represents a gene coding for a polypeptide which represses transcription from the repA promoter between the copB and copA genes; copA represents a gene coding for an RNA molecule and inhibits translation of RepA-mRNA; repA represents a gene coding for a protein required for plasmid R1 replication; ori denotes the vegetative origin of replication; aphA represents a gene encoding resistance to kanamycin; bla represents a gene encoding resistance to ampicillin; lacA, lacY and lacZ represent the inserted lac operon, of which lacA codes for transacetylase, lacY codes for permease and lacZ codes fpr β-galactosidase; cI$_{857}$ represents a gene coding for a temperature-sensitive repressor of the λP$_R$ promoter; tnpR and tnpA represent genes coding for Tn3 transposition functions, par represents the region responsible for plasmid partitioning; recA represents a gene coding for a recombination protein; and PrecA represents the recA promoter. Below the horisontal line, the sites for restriction enzymes are shown in which P denotes PstI; B$_2$ denotes BglII; S$_1$ denotes SalI; E denotes EcoRI; H$_3$ denotes HindIII; B$_1$ denotes BamHI; B$_2$B$_1$ denotes a fusion of a BglII site and a BamHI site; and C denotes ClaI. In FIG. 11, the plasmid depicted is drawn on the same scale as the plasmids in the other figures, and the bracketed insertion represents the inserted lac genes.

Preferred embodiments of the invention are described in the following examples:

MATERIALS AND METHODS

The strain of *Escherichia coli* K-12 used was CSH50 (Δpro-lac, rpsL; cf. J. Miller: *Experiments in Molecular Genetics*, Cold Spring Harbor Laboratory, Cold Spring Harbor, N.Y., 1972). Several plasmids (Table 1) and bacteriophages (Table 2) were used.

The experimental techniques used were standard techniques employed in the fields of microbial genetics (J. Miller: *Experiments in Molecular Genetics*, Cold Spring Harbor, N.Y., 1972) and genetic manipulation (Davis, Botstein and Roth: *A Manual for Genetic Engineering; Advanced Bacterial Genetics*, Cold Spring Harbor, N.Y., 1980).

All cells were grown in LB medium (Bertani, J. Bact. 62, 1951, 293) or in A+B minimal medium (Clark and Maaløe, J. Mol. Biol. 23, 1967, 99), and the plates used were LA plates containing LB medium and 1.5% of agar. Preparation and analysis of plasmid DNA was performed using dye boyant density gradient centrifugation according to the method described by Stougaard & Molin, Anal. Biochem. 118, 1981, 181. Labelling of DNA and preparation of lysates for the determination of plasmid content was performed according to Molin et al., J. Bact. 138, 1979, 70. The relative content of plasmid DNA was measured as amounts of labelled thymidine present in the plasmid band relative to that in the chromosomal band in the gradients.

The resstriction endonucleases employed in the examples were used in accordance with the prescriptions provided by the manufacturer. The partial restrictions were performed with a ten-fold dilution of the enzymes.

In addition, the following screening methods were employed:

1. Screening for λ immunity (immλ+)

In all the examples described, the cI$_{857}$ mutant allele is used. Plasmids carrying this gene make the hose *E. coli* cell resistant to infection with lytic λ phages at 30° C. To select resistant cells more than 10$^8$ λb2 phage particles are added to plates before spreading the bacteria. Surviving colonies are further tested for their plasmid content.

2. Screening for copB+

Genetic fusions between the repA promoter and the lac operon from which the lac promoter has been deleted are constructed and inserted into a p15 plasmid (pGA46). One resulting hybrid plasmid, pJL217, is responsible for a Lac+ phenotype when harboured by a Δlac host E. coli strain.

The Lac+ phenotype is easily detected on McConkey lactose indicator plates (red colonies). The presence of a copB+ gene in cells harbouring pJL217 results in a Lac− phenotype which appears as white colonies on the indicator plates. Thus, copB+ hybrids are easily scored as Lac− colonies when plasmid DNA is transformed to E. coli Δlac cells that harbour plasmid pJL217.

TABLE 1
Plasmids used

| Plasmid | Source |
| --- | --- |
| pKN1562 | S. Molin et al., J. Bact., 138, 1979, pp. 70–79. |
| pBR322 | F. Bolivar et al., Gene 2, 1977, p. 95. |
| pJL217 | Constructed by inserting a Sau3A fragment from pKN1562 carrying the repA promoter in the BglII site of pJL207, a hybrid plasmid carrying lac genes without the lac promoter. |
| pOU16 | Light & Molin, Mol. Gen. Genet. 184, 1981, p. 57. |
| pGA46 | An & Friesen, J. Bact. 140, 1979, pp. 400–407. |
| pMC903 | Casadaban et al., J. Bact. 143, 1980, p. 971. |
| pMC871 | Casadaban et al., op. cit., 971. |
| pVH1424 | Constructed by P. Valentin-Hansen by insertng a Sau3A fragment carrying the deo promoter from plasmid pVH17 (Valentin-Hansen et al., EMBO J., 1982, 317) in the BamHI side of plasmid pMC1403 (Casadaban et al., op. cit., 971). |
| pSKS104 | Constructed by M. Casadaban by inserting a PvuII fragment containing the lac promoter and translation initiation region from pM13mp7 (Messing et alk., Nucleic Acids Res. 9, 1981, 309) in the SmaI site of pMC1403, followed by homologous recombination between the lacZ segments. |
| pKN184 | Nordstrom et al., Plasmid 4, 1980, 322. |
| pJL3 | Molin et al., Mol. gen. Genet. 181, 1981, 123–130. |
| pVH1451 | Valentin-Hansen et al., op. cit. |
| pBEU14 | Uhlin & Clark, J. Bact. 148, 1981, 386–90 |
| pMC1403 | Casadaban et al., J. Bact. 143, 1980, 971 |

TABLE 2
Bacteriophages Used

| Phage | Source |
| --- | --- |
| EDλ4 | Dempsey & Willetts, J. Bact. 126, 1976, p. 166. |
| EDλTn3 | Nordstrom, Molin, Aagaard-Hansen Plasmid, 4, 1980, pp. 215–27 |

Parent plasmids

Plasmid pKN1562 is a derivative of plasmid R1, in all essentials constructed as described in Molin et al.: "Clustering of Genes Involved in Replication, Copy Number Control, Incompatibility, and Stable Maintenance of the Resistance Plasmit R1drd-19", J. Bact. 138, 1979, pp. 70–79, except for a few modifications added by later research. pKN1562 has a molecular weight of $6.9 \times 10^6$ daltons and the following genotype: copA+, copB+, repA+, aphA+, Δpar (see FIG. 3). It carries resistance to kanamycin. The plasmid possesses the replication properties of the wild-type plasmid, has a copy number of 3–5 per fast growing cell and is lost with a frequency of 1% per generation due to the lack of the par gene (the gene for partitioning).

By restricting pKN1562 with BglII to delete part of the copB gene and ligating the sticky ends, another plasmid, pJL20, is constructed. The molecular weight of this plasmid is $6.7 \times 10^6$ daltons and its genotype is as follows: copA+, ΔcopB, repA+, aphA+, Δpar. The plasmid has a copy number of 35–40 per fast growing cell, and there is no loss of the plasmid. This plasmid, too, mediates resistance to kanamycin.

Plasmid designation

It should be noted that the plasmids designated pJEL . . . in the examples and drawing of the basic application have renamed pOU . . . in the present application.

EXAMPLE 1

Construction and characterization of pOU51

DNA from plasmid pJL20 and phage EDλ4 was prepared according to standard methods. Plasmid and phage DNA was mixed at a final concentration of 20 μg/ml of each and in a final volume of 100 μl, restricted with GblII for 30 minutes, heat inactivated at 70° C. for 10 minutes, and ligated with T4 DNA ligase overnight at 15° C. Aliquots of the ligation mixture were transformed to E. coli strain CHS50. Transformants were selected on plates containing 50 μg/ml kanamycin onto which a suspension with about $10^9$ λb2 particles has been spread. The plates were incubated for 20 hours at 30° C.

Surviving colonies were reisolated and tested for resistance to λb2 by cross-streaking at 30° C., for growth at 42° C. by streaking on Km plates at 42° C., and for the molecular weight of the plasmid by preparing plasmid DNA and analysing on agarose gels.

In this way a plasmid, pOU51, was found which mediates resistance to Km and to λ infection, renders the host bacteriumn temperature-sensitive for growth, and has an insertion of phage DNA in jPL20 corresponding to about $1.6 \times 10^6$ daltons. The total molecular weight of the plasmid was $8.4 \times 10^6$ daltons. These properties are all carried by the plasmid since new E. coli recipient strains acquire all the plasmid's phenotypic properties when transformed with pOU51 DNA.

DNA was prepared fromn pOU51 and the plasmid mapped with restriction enzymes by purifying the plasmid DNA, cleaving it with restriction enzyme(s) and analysing the resulting fragments by means of agarose gel electrophoresis (cf. FIG. 4). In this way the inserted $1.6 \times 10^6$ dalton fragment was identified as a BglII fragment from phage λ carrying the cI repressor gene (responsible for λ immunity at 30° C.) and the λP$_R$ promoter, and the orientation of the inserted fragment was determined to be as shown in FIG. 4. From the restriction map it further appears that a pOU51 has a unique site for the restriction endonuclease EcoRI which makes it possible to use the plasmid as a cloning vector.

The effect of the plasmid on the growth of the cells was investigated by growing a culture in medium at 30° C. At a time when growth was exponential the temperature was shifted to 42° C. and cell growth followed (determined spectrophotometrically). Within 1.5–2 hours of growth at 42° C. the culture ceased to grow.

The plasmid DNA content was measured as described in MATERIALS AND METHODS from 10 ml cultures growing in A+B minimal medium supplemented with 0.2% of glucose and 1% of casamino acids. One 10 ml culture was labelled with 50 μCi of $^3$H-thymidine at 30° C., the other received the isotope just after a shift to 42° C. until the cells ceased to grow. The relative content of plasmid DNA was 2% at 30° C. corresponding to 25–40 plasmid copies per cell. At 42° C. the relative content was more than 50% corresponding to more than 1000 plasmid copies per cell.

The properties of this plasmid are shown in Table 5.

The strain of E. coli CSH50/pOU51 is deposited in the German Collection of Microorganisms (Deutsche Sammlung von Mikroorganismen, Grisebachstrasse 8, D-3400 Göttingen), in the following abbreviated to DSM, under the Accession No. 2467.

EXAMPLE 2

Construction and characterization of pOU53

By using the plasmid described in Example 1 as a starting material and by partially restricting pOU51 with HindIII, the title plasmid was constructed from which the gene for encoding kanamycin resistance had been deleted, but which had retained the gene for encoding λ immunity. The plasmid was transformed to E. coli strain CHS50. pJEL53 had a molecular weight of $3.2 \times 10^6$ daltons and the following genotype: copA+, ΔcopB, repA+, Δpar, immλ$^{30}$, ΔaphA.

Figure 5:
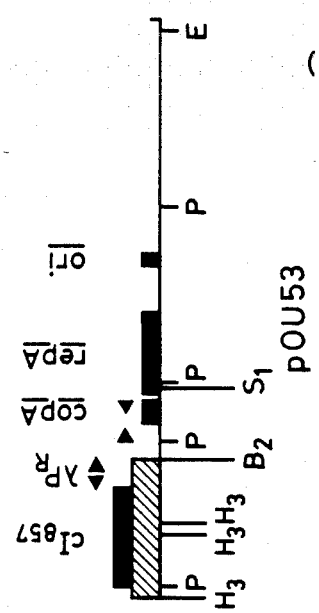

The plasmid was mapped with restriction enzymes as described in Example 1 (cf. FIG. 5). From the restriction map it appears that pOU53 has a unique site for the restriction endonuclease EcoRI which makes it possible to use the plasmid as a cloning vector.

To demonstrate the presence of the desired plasmid in the host cells, cell cultures were grown on plates containing λb2 phage particles as described above to test for resistance to λ infection. The cells were further tested for sensitivity to kanamycin by replica plating colonies on plates containing 50 μg/ml Km. To test for temperature-sensitive growth, the cells were streaked on plates at 42° C. and grown in the manner described in Example 1.

When the plasmid DNA content was measured in the manner described in Example 1, the cells were found to contain 20–40 plasmid copies at 30° C. and more than 1000 plasmid copies at 42° C. There was no loss of the plasmid.

The properties of this plasmid are shown in Table 5.

The strain of E. coli CSH50/pOU53 is deposited in the DSM under the Accession No. 2468.

EXAMPLE 3

Construction and characterization of pOU56

By in vivo insertion of the Tn3 transposon from a λ::Tn3 phage including the genes for transposition and ampicillin resistance (β-lactamase) (Nordström, Molin and Aagaard-Hansen, Plasmid 4, 1980, 215–227) in pOU53, the title plasmid was constructed. Plasmid DNA was isolated from a strain carrying the λTn3 phage in the chromosomes and plasmid pOU53. The plasmid DNA was transformed to E. coli strain CSH50 selecting for ampicillin resistance and λ immunity. pOU56 had a molecular weight of $6.5 \times 10^6$ daltons and the following genotype: copA+, ΔcopB, repA+, ΔaphA, immλ+, bla+ (::Tn3).

Figure 6:
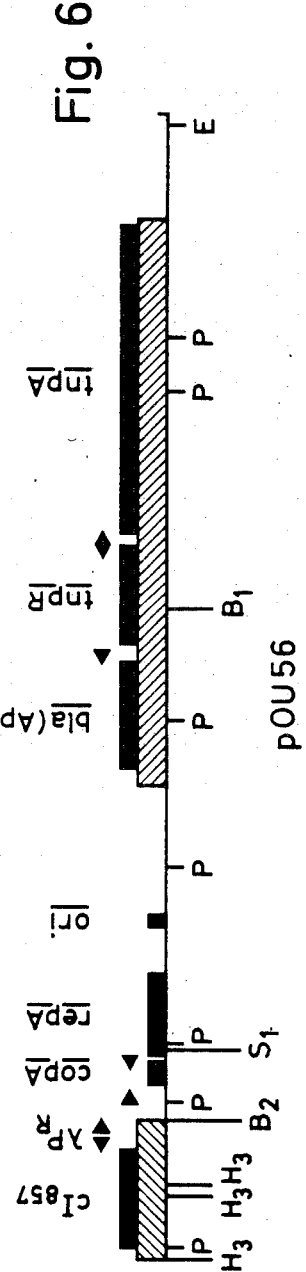

The plasmid was mapped with restriction enzymes as described in Example 1 (cf. FIG. 6). The restriction map shows where the Tn3 transposon has been inserted in pOU56, and further shows that the plasmid has a unique site for each of the restriction endonucleases EcoRI and BamHI. While the plasmid is useful as a starting material for preparing the plasmid pOU57 (cf. Example 4 below), it is not preferred as a cloning vector as, due to the predsence of the transposition gene, antibiotic resistance may be transferred to other bacteria.

To demonstrate the presence of the desired plasmid in the host cell, cell cultures were grown on plates containing λb2 phage particles as described above to test for resistance to λ infection. The cells were further tested for ampicillin resistance on plates containing 50 μg/ml ampicillin. The test for temperature-sensitive growth was performed in the manner described above.

pOU56 was found to have the same replication properties as pOU53.

The properties of this plasmid are shown in Table 5.

The strain of E. coli CSH50/pOU56 is deposited in the DSM under the Accession No. 2469.

EXAMPLE 4

Construction and Characterization of pOU57 (a type A plasmid)

In order to eliminate the possibility of transposition of Tn3 from plasmid pOU56 due to its carrying the entire transposon, the plasmid was cleaved at the BamHI and EcoRI sites to delete the transposition gene whereas the gene coding for β-lactamase was retained. In order to effect annealing of the sticky ends, a small BamHI-EcoRI fragment from palsmid pBR322 was inserted, thus producing plasmid pOUL57. The plasmid was transformed to E. coli strain CSH50. pOU57 had a molecular weight of $4.2 \times 10^6$ daltons, and the following genotype: copA+, ΔcopB, repA+, Δpar, ΔaphA, immλ+, bla+ (ΔTn3).

The plasmid was mapped with restriction enzymes as described in Example 1 (cf. FIG. 7). From the restriction map it appears that pOU57 has unique sites for each of the restriction endonucleases BamHI and EcoRI which makes it useful as a cloning vector.

To demonstrate the presence of the desired plasmid in the host cell, cell cultures were grown on plates containing λb2 phage particles as described above to test for resistance to phage infection. The cells were further tested for ampicillin resistance in the manner described above. The molecular weight of the plasmid was determined by means of agarose gel electrophoresis. The test for temperature-sensitive growth was performed in the manner described above.

pOU57 was found to have the same replication properties as pOU53.

The properties of this plasmid are shown in Table 5.

The strain of E. coli CSH50/pOU57 is deposited in the DSM under the Accession No. 2470.

EXAMPLE 5

Construction and Characterization of pOU71 (a type B plasmid)

By using the plasmid described in Example 4 as a starting material and by inserting a BglII fragment from pKN1562 including part of the copB gene in the BglII site of pOU57, the title plasmid was constructed which carried both the cI-λP$_R$ repressor-promoter system and the wild-type gene for the copB inhibitor of R1-type plasmids. The plasmid was transformed to E. coli strain CSH50. The molecular weight of pOU71 was $4.3 \times 10^6$ daltons and the genotype was as follows: copA+, copB+, repA+, Δpar, ΔaphA, immλ+, bla+.

The plasmid was mapped with restriction enzymes as described in Example 1 (cf. FIG. 8). From the restriction map it appears that pOU71 has the same unique restriction sites as pOU57.

To demonstrate the presence of the desired plasmid in the host cell, cell cultures were tested for resistance to λ infection and ampicillin resistance in the manner described above. The plasmids were then screened for the presence of the copB gene by means of the method described in the section entitled "Screening for copB+". The test for temperature-sensitive growth was carried out in the manner described above. Finally, the number of plasmid copies at 30° C. was determined by means of radio labelling and gradient centrifugation.

When the content of plasmid DNA was measured in the manner described in Example 1, the cells were found to contain 3-5 plasmid copies at 30° C. and more than 1000 plasmid copies at 42° C. At 30° C., the plasmid was lost with a frequency of 1% per generation.

The properties of this plasmid are shown in Table 5.

The strain of E. coli CSH50/pOU71 is deposited in the DSM under the Accession No. 2471.

EXAMPLE 6

Construction and Characterization of pOU73 (a type C plasmid)

By using the plasmid described in Example 4 as a starting material and by inserting an EcoRI fragment from pOU16 carrying the copB gene in the EcoRI site of pOU57, the title plasmid was constructed having the gene for the copB inhibitor as well as the cI-λP$_R$ repressor-promoter system. The plasmid was transformed to E. coli strain CSH50. pOU73 had a molecular weight of $4.4 \times 10^6$ daltons and the following genotype: copA+, copB+, repA+, Δpar, ΔaphA, immλ+, bla+.

The plasmid was mapped with restriction enzymes as described in Example 1 (cf. FIG. 9). From the restriction map it appears that the copB gene has been inserted in a region of the plasmid where it is not naturally located. It further appears that the plasmid has a unique site for the restriction endonuclease BamHI so that it may be used as a cloning vector.

The same screening methods as for pOU71 were employed.

When the content of plasmid DNA was measured in the manner described in Example 1, the cells were found to contain 0.5-1 plasmid copy at 30° C. and more than 1000 plasmid copies at 42° C. At 30° C., the plasmid was lost with a frequency of more than 5% per generation.

The properties of this plasmid are shown in Table 5.

The strain of E. coli CSH50/pOU73 is deposited in the DSM under the Accession No. 2472.

EXAMPLE 7

Construction and characterization of pOU75 (a type B plasmid)

By using the plasmid described in Example 5 as a starting material and by partially restricting pOU71 with HindIII, the title plasmid was constructed from which the EcoRI site had been deleted. The plasmid was performed to E. coli strain CSH50. pOU75 has a molecular weight of $4.2 \times 10^6$ daltons and the following genotype: copA+, copB+, repA+, Δpar, ΔaphA, immλ+, bla+.

The plasmid was mapped with restriction enzymes as described in Example 1 (cf. FIG. 10). From the restriction map it appears that the deletion of the HindIII fragment results in the removal of the EcoRI site of pOU71.

To demonstrate the presence of the desired plasmid in the host cell, cell cultures were tested for resistance to λ infection and ampicillin resistance, as well as temperature-sensitive growth in the manner described above. The plasmid was also tested for loss of the EcoRI site by restricting with the enzyme.

pOU75 was found to have the same replication properties as pOU71.

The properties of this plasmid are shown in Table 5.

The strain of E. coli CSH50/pOU75 is deposited in the DSM under the Accession No. 2473.

EXAMPLE 8

Gene product amplification

Plasmid pMC903 (Casadaban et al., J. Bact. 143, 1980, 971) was cleaved with the restriction enzymes BamHI and BglII producing a BamHI-BglII fragment carrying lac genes. Plasmid pOU71 was cleaved with BamHI, and the BamHI-BglII fragment obtained above was inserted at this site as shown in FIG. 11 followed by ligation with T4 DNA ligase, thus producing the plasmid pOU106 which was transformed to E. coli strain CSH50. The cells were streaked onto McConkey lactose indicator plates (see J. Miller, Experiments in Molecular Genetics, Cold Spring Harbor, 1972) containing 50 μg/ml ampicillin and incubated at 30° C. to select for red colonies (Lac+). The temperature was then shifted to 42° C., and the amplification of gene product (β-galactosidase) was measured as shown in Table 3. The measuring was performed according to the method described by J. Miller, op cit.

TABLE 3

| Amplification of gene product | | | |
|---|---|---|---|
| Plasmid of the Invention | | Prior Art Plasmid (pKN410) | |
| Minutes after shift to 42° C. | Accumulated relative specific activity[1] of gene product[2] | Minutes after shift to 42° C. | Accumulated relative specific activity of gene product[3] |
| 0 | 10 | 0 | 10 |
| 10 | 21 | | |
| 25 | 34 | | |
| 55 | 62 | 60 | 20 |
| 83 | 107 | 90 | 47 |

[1]Enzyme activity per total amount of protein, i.e. the increase of β-galactosidase per cell.
[2]β-galactosidase mediated by plasmid pOU106.
[3]β-lactamase mediated by plasmid pKN410 (Uhlin et al., Gene 6, 1979, Table II, p. 100).

From the table it appears that the level of gene product amplification is comparable to that obtained with other runaway vectors (e.g. Uhlin et al., Gene 6, 1979, 91-106).

The promoter from which the β-galactosidase gene is expressed is the cI promoter and/or the tetracycline promoter located on the DNA fragment from pBR322 which, although it is relatively weak, cannot be dismissed as an influencing factor and which transcribes in the same direction as the cI promoter.

pOU106 was mapped with restriction enzymes as described in Example 1 (cf. FIG. 11). From the restriction map it appears that the plasmid has a unique site for the restriction endonuclease BamHI immediately downstream of the inserted lac genes, which makes the plasmid useful as a cloning vector.

The properties of this plasmid are shown in Table 5.

The strain of E. coli CSH50/pOU106 is deposited in the DSM under the Accession No. 2474.

EXAMPLE 9

Construction and characterization of pOU79 (a type B plasmid)

Plasmid pOU71 was cleaved completely with BamHI and partially with PstI and ligated with a DNA fragment (carrying the lac operon) from plasmid pMC871 (Casadaban et al., J. Bact. 143, 1980, 971) which had been cleaved completely with BamHI and PstI.

The ligation mixture was transformed to E. coli strain CSH50 selecting for resistance to ampicillin on McConkey lactose indicator plates containing 50 μg/ml ampicillin which were incubated at 30° C. After 20 hours' incubation at 30° C., the plates were incubated for a short period (1-2 hours) at 42° C., and colonies that shifted from a Lac− (white) to a Lac+ (red) phenotype were further analysed. The title plasmid was identified from one such colony. pOU79 had a molecular weight of $8.8 \times 10^6$ daltons and the following genotype: copA+, copB+, repA+, Δpar, immλ+, bla+, lac+.

The plasmid was mapped with restriction enzymes as described in Example 1 (cf. FIG. 12). From the restriction map it appears that the plasmid has a uniqaue site for the restriction endonuclease BamHI just upstream of the lac genes. Insertion of promoter-carrying DNA fragments in the proper orientation at this site results in transcription of the lac genes thus giving rise to a Lac+ phenotype of cells carrying such hybrid plasmids at 30° C. Lac+ cells are easily identified on McConkey lactose indicator plates.

The plasmid also has a unique site for the restriction endonuclease EcoRI located at one end of the lacZ gene. Insertion of EcoRI fragments at this site eliminates the activity of the lacZ gene product, β-galactosidase, resulting in a Lac− phenotype which is easily scored as the formation of colourless colonies on McConkey lactose indicator plates after a temperature shift from 30° C. to 42° C. (cf. the description above). The plasmid is thus useful as a cloning vector.

pOU79 was found to have the same replication properties as pOU71.

The properties of this plasmid are shown in Table 5.

The strain of E. coli CSH50/pOU79 is deposited in the DSM under the Accession No. 2481.

EXAMPLE 10

Construction and characterization of pOU82 (a type B plasmid)

Plasmid pOU79 was cleaved completely with BamHI and partially with SalI, and a BamHI-SalI fragment from pSKS104 carrying the lac operon from which the lac promoter had been deleted and the first four codons of the lacZ gene was inserted to construct pOU80 (not shown).

pOU80 is Lac− and has a BamHI site and an EcoRI site just upstream of the lac genes. Moreover, the EcoRI site normally found in the lacZ gene is missing since the lac genes in pSKS104 are derived from pMC104 (Casadaban et al)., J. Bact. 143, 1980, 971).

The title plasmid was constructed by replacing an EcoRI-ClaI fragment in the lacZ gene (cf. the map of pOU79, FIG. 12) of pOU80 with an EcoRI-ClaI fragment from pVH1424 carrying the deo promoter and the amino terminal end of the lacZ gene. The replacement results in a reconstruction of the lacZ gene and, due to the presence of the deo promoter, the resulting hybrid plasmid, pOU82, mediates a Lac$^{30}$ phenotype when transformed to E. coli strain CSH50. pOU82 had a molecular weight of $8.1 \times 10^6$ daltons and the following genotype: copA+, copB+, repA+, Δpar, immλ+, bla+, lac+.

The plasmid is eventually lost from the cells at 30° C. due to the lack of the par region, which is easily observed on non-selective McConkey lactose indicator plates (cf. Example 11).

The plasmid was mapped with restriction enzymes as described in Example 1 (cf. FIG. 13). From the restriction map it appears that the plasmid has a unique site for each of the restriction endonucleases EcoRI and BamHI, which makes it possible to use the plasmid as a cloning vector.

pOU82 was found to have the same replication properties as pOU71.

The properties of this plasmid are shown in Table 5.

The strain of E. coli CSH50/pOU82 is deposited in the DSM uner the Accession No. 2482.

EXAMPLE 11

Construction and characterization of pOU91 (a type B plasmid)

To construct a plasmid which is stable with respect to partitioning, pOU82 was cleaved with EcoRI, and the EcoRI-A fragment including the wild-type par region of a plasmid R1 derivative, pKN184 (Nordström et al., Plasmid 4, 1980, 322), was inserted at this site followed by ligation. The resulting plasmid (pOU90), not shown) was transformed to E. coli strain CSH50, and the cells were grown selectively on plates containing 50 μg/ml ampicillin at 30° C. As a control, cells containing pOU82 were grown in a similar manenr to ensure the presence of the plasmids in both starting colonies. Next, samples of both colonies were streaked on plates not containing any antibiotic, and the cells were left to grow for 25 cell generastions. To screen for the stable inheritance of the Lac+ phenotype, cells from both the resulting colonies were streaked onto McConkey lactose indicator plates at 30° C. where the cells to which pOU90 had been transformed generated red colonies which showed that this plasmid had been retained, while the control cells to which pOU82 had been transformed generated both red and colourless colonies which means that, during the selection-free period, pOU82 had been lost from some of the cells.

The intermediate plasmid, pOU90, was then cleaved completely with BamHI and partially with Sau3A to reduce the size of the plasmid, thus producing the title plasmid. After transformation to E. coli strain CSH50, plasmid stability was determined in the manner described above. pOU91 had a molecular weight of $12.5 \times 10^6$ daltons and the following genotype: copA+, copB+, repA+, par$^{30}$, immλ+, bla+, lac$^{30}$.

Figure 14:
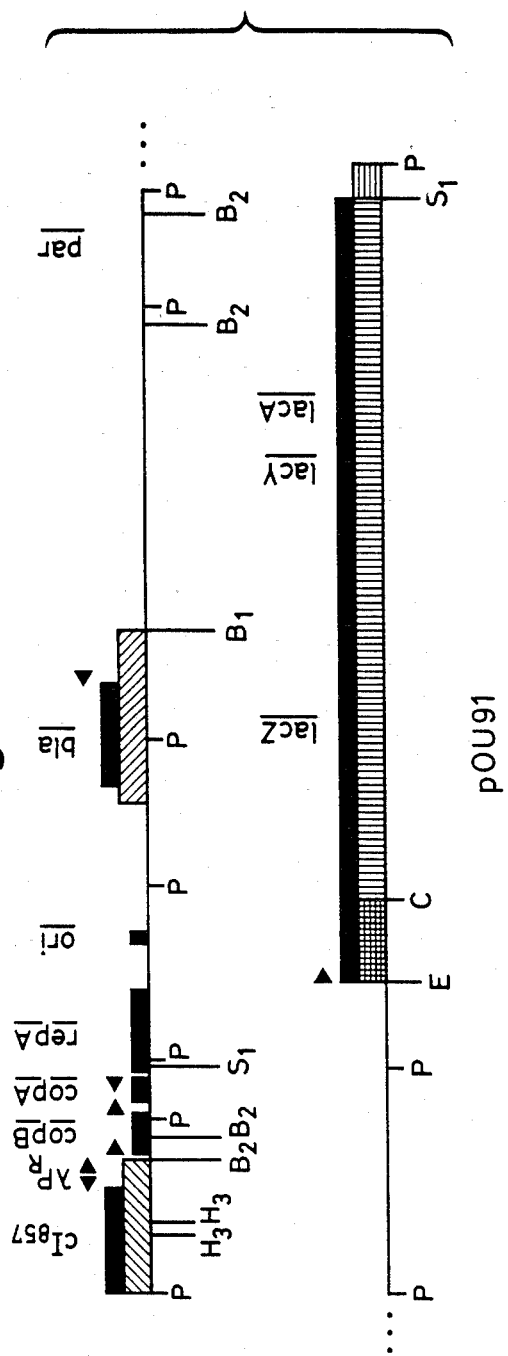

The plasmid was mapped with restriction enzymes as described in Example 1 (cf. FIG. 14). From the restriction map it appears that pOU91 has unique sites for each of the estriction endonucleases EcoRI and BamHI, which makes the plasmid useful as a cloning vector.

pOUL91 was found to have the same replaction properties as pOU71 but, on contradistinction to pOU71, the plasmid is completely stable at 30° C.

The properties of this plasmid are shown in Table 5.

The strain of E. coli CSH50/pOU91 is deposited in the DSM under the Accession No. 2483.

EXAMPLE 12

Construction and characterization of pOU101 (a type B plasmid)

By using the plasmid described in Example 7 as a starting material and by inserting a Sau3A fragment carrying the gene coding for chloramphenicol acetyl transferae (cat+) in the BamHI site of pOU75, the title plasmid was constructed with conferred chloramphenicol resistance to the host cell. The plasmic was transformed to E. coli strain CSH50. pOU101 had a molecular weight of $4.7 \times 10^6$ daltons and the following genotype: copA+, repA+, $\Delta$par, $\Delta$aphA, imm$\lambda$+, bla+, cat+.

Figure 15:
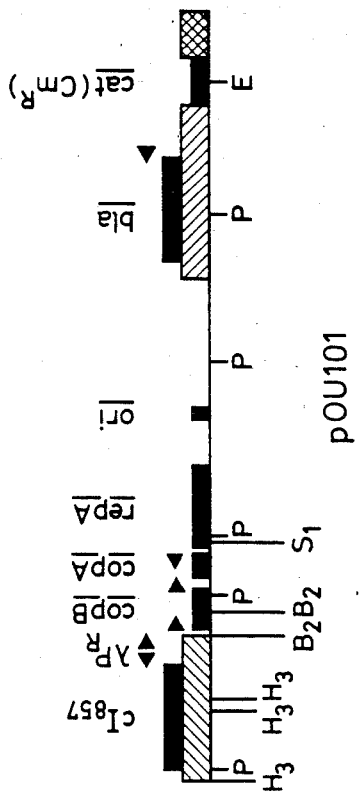

The plasmid was mapped with restriction enzymes as described in Example 1 (cf. FIG. 15). From the restrictio map it appears that pOU101 has a unique site for the restriction endonculease ECoRI which makes it possible to use the plasmid as a cloning vector. Moreover, inserton of EcoRI fragments inactivates the cat+ gene allowing screening for EcoRI hybrids.

To demonstrate the presence of the desired plasmid in the host cell, cell cultures were tested for resistance to $\lambda$ infection and ampicillin resistance in the manner described above. Further, the cells were tested for resistance to chloramphenicol by growing cultures on plates containing 20 $\mu$g/ml chloramphenicol. The cells were also tested for temperature-sensitive growth in the manner described above. pOU101 was found to have the same replication properties as pOU71.

The properties of this plasmid are shownin Table 5.

The strain of E. coli CSH50/pOU101 is deposited in the DSM under the Accession No. 2757.

EXAMPLES 13

Construction and Characterization of pOU110

The EcoRI - ClaI fragment containing part of the lacZ gene was deleted from plasmid pOU80 (described in Example 10; cf. the map of pOU79, FIG. 12) and replaced wit an EcoRI - ClaI fragment from plasmid pVH1451 (Valentin-Hansen et al., the EMBO Journal 1, 1982) carrying the deo promoter and the amino terminal end of the lacZ gene. The resulting plasimid was denoted pOU83 (cf. FIG. 16).

Plasmid pOU83 was partially restricted with BamHI and BglII in order to delete the lac genes adn the DNA fragment carrying the cl repressor gene and the $\lambda P_R$ promoter. After ligation and transformation to CSH50, a plasmid with the desired properties was isolated, resulting in a close fusion of the deo promoter and the copB gene. The plasmid, denoted pOU110, had a molecular weight of $3.2 \times 10^6$ daltons and the following genotype: copA+, copB+, repA+, $\Delta$par, bla+.

The plasmid was mapped with restriction enzymes as described in Example 1 (cf. FIG. 17). From the restriction map it appears that the plasmid had a unique site for each of the restriction endonucleases EcoRI and BamHI which makes it possible to use the plasmid as a cloning vector.

When cultures of E. coli strain S$\phi$929 (cytR, lac, deo; recA), to which pOU110 had been transformed, were grown overnight in LB medium without glucose, uncontrolled plasmid replication occurred at a cell density of above $2 \times 10^8$ cells/ml.

The strain of E. coli CSH50/pOU110 is deposited in the DSM under the Accession No. 2758.

EXAMPLE 14

Construction and Characaterization of pOU130

Plasmid pOU91 was cleaved with BamHI and the BamHI site was deleted by means of the exonculease Bal31 to produce plasmic pOU92 (not shown). The plasmic was restricted with EcoRI and ClaI and a corresponding EcoRI - ClaI fragment from plasmid pMC1403 (Casadaban et al., J. Bact 143, 1980, 971) was inserted to produce plasmid pOU93 which carried the lac operon without the deo promoter. At the BamHI site thus produced a BglII fragment carrying a copB gene was inserted to produce pOU130 (cf. FIG. 18) followed by ligation and transformation to E. coli strain CSG50. The cells were streaked onto McConkey lactose indicator plates containing 50 $\mu$m/ml ampicillin and incubated at 30° C. to select for red colonies (Lac+). The temperature was then shifted to 42° C., and the amplification of $\beta$-galactosidase is shown in Table 5. After 45 minutes of incubation at 42° C., the temperature was lowered to below 38° C. The $\beta$-galactosidase amplification measured after the temperature shift is shown in Table 5.

TABLE 4

| | Expression of $\beta$-galactosidase from pOU130 after amplification of plasmid DNA | |
|---|---|---|
| Growth conditions | $^d$Spec. act. of $\beta$-galactosidase | Amplification factor |
| $^a$30° C.; steady state | 0.03 | 1 |
| $^b$30° C.  42° C. | 0.7 | 23 |
| $^c$30° C.  42° C.  37° C. | 2.5 | 83 |

$^a$Cells of CSH50 harbouring pOU130 grown exponentially in LB medium at 30° C.
$^b$After exponential growth at 30° C. the culture was shifted to 42° C., at which temperature growth was continued for 2 hrs.
$^c$After exponential growth at 30° C. the culture was shifted to 42° C. for 45 minutes, after which it was shifted to 37° C. for 90 minutes.
$^d$See Materials and Methods. Specific activities of $\beta$-galactosidase are expressed as described by Light and Molin, Mol. Gen. Genet. 1981, (pp 56–61).

From the table it appears that gene product amplification is considerably improved when employing a shift back to a lower temperature, thus demonstrating that this method is particularly useful to obtain a maximum expression of the gene products in question.

As $\beta$-galactosidase is constitutively expressed from such a gene fusion (Light & Molin, J. Bact. 151, 1982, 1129–1135), the levels of enzyme activity accurately reflect the gene product amplification capacity of the plasmids of the invention.

The strain of E. coli CHSD50/pOU130 is deposited in the DSM under the Accession No. 2759.

EXAMPLE 15

Construction and characterization of pIC31 pOU75 was cleaved with BamHI, and a BamHI fragment from plasmid pBEU14 (Uhlin and Clark, J. Bact. 148, 1981, 386–90) carrying the recA promoter and gene was inserted followed by transformation to E. coli strain CSG50. The title plasmid had a molecular weight of $6.3 \times 10^6$ daltons and the following genotype: recA., bla+, copA+, copB+, repA+, imm$\lambda$+.

The plasmid was mapped with restriction enzymes as described in Example 1 (cf. FIG. 19). From the restriction map it appears that pLC31 contains a unique site for the restriction enzyme EcoRI downstream of the recA promoter suitable for the insertion of foreign genes.

pLC31 was found to have the same replication properties as pOU71.

When cells containing pLC31 were grown at 30° C., the promoter remained fully repressed, while after a temperature shift to 42° C., the lexA repressor was gradually titrated and transcription from recA was initiated leading to an amplified production of recA gene product which could be detected by polyacrylamide gel electrophoresis.

The properties of this plasmid are shown in Table 5.

The strain of E. coli CSH50/pLC31 is deposited in the DSM under the Accession No. 2718.

EXAMPLE 16

Construction and characterization of pLC33

Plasmid PLc28 (Remaut et al., Gene 15, 1981, pp. 81-93) carrying the $\lambda P_L$ promoter and the bla gene and provided with a linker comprising the restriction sites EcoRI, SmaI, BamHI, SalI, PstI and HindlII, was cleaved with EcoRI and inserted in the EcoRI site of plasmid pOU51 (cf. Example 1) followed by ligation and transformation to E. coli strain CSH50. This plasmid, pLC32', (cf. FIG. 20), which had a molecular weight of $10.6 \times 10^6$ daltons, was digested with BanHI and with the exonculease Bal31 to delete the linker under the conditions described in T. Maniatis et al., Molecule Cloning, A Laboratory Manual, Cold Spring Harbor Laboratory, Cold Spring Harbor, N.Y., 1982, pp. 135-139, followed by religation and transformation to E. coli strain C600 (R. K. Appleyard, Genetics 39, 1954, pp. 440-452) selecting for plasmids which are kanamycin and ampicillin resistant. The resulting plasmid was denoted pLC33 and had a molecular weight of $10.3 \times 10^6$ daltons and the following genotype: copA+, copB−, repA+, aphA+, imm$\lambda$+, bla+.

The plasmid was mapped with restriction enzymes as described in Example 1 (cf. FIG. 22). From the restriction map it appears that the $\lambda P_L$ promoter is located immediately upstream of the unique EcoRI site which makes the plasmid convenient as a cloning vector.

pLC33 was found to have the same properties as pOU51.

The properties of thsi plasmid are shownin Table 5.

The strain of E. coli C600/pLC33 is deposited in the DSM under the Accesson No. 2945.

EXAMPLE 17

Construction and characterization of pLC34

Plasmid PLc28 (Remaut et al., Gene 15, 1981, pp. 81-93) carrying the $\lambda P_L$ promoter and the bla gene and provided with a linker comprising the restriction sites EcoRI, SmaI, BamHI, SalI, PstI and HindlII, was cleaved with EcoRI and inserted in the EcoRI site of plasmid pOU51 (cf. Example 1) followed by ligation and transformation to E. coli strain CSH50. This plasmid, pL32', (cf. FIG. 20), which had a molecular weight of $10.6 \times 10^6$ daltons, was digested with BalHI and with the exonculease Bal31 to delete the bla gene under the conditions described in T. Maniatis et al., Molecular Cloning, A Laboratory Manual, Cold Spring Harbor Laboratory, Cold Spring Harbor, N.Y., 1982, pp. 135-139, followed by religation and transformation to E. coli strain C600 (R. K. Appleyard, Genetics 39, 1954, pp. 440-452) selecting for plasmids which are kanamycin resistant and ampicillin sensitive. The resulting plasmid was denoted pLC34 and had a molecular weight of $8.4 \times 10^6$ daltons and the folowing genotyupe: CopA+, copB−, repA+, aphA+, imm$\lambda$+.

The plasmid was mapped wit restriction enzymes as described in Example 1 (cf. FIG. 23). From the restriction map it appears that the $\lambda P_L$ promoter is located immediately upstream of the unique EcoRI site which makes the plasmid convenient as a cloning vector.

pLC34 was found to have the same replcation properties as pOU51.

The properties of this plasmid are shown in Table 5.

The strain of E. coli C600/pLC34 is deposited in the DSM under the Accession No. 2946.

TABLE 5

Properties of miniR1-$\lambda P_R$ plasmids as cloning vectors

| Plasmid | Relevant phenotype | Unique restriction site(s) | Screening (insertional inactivation) | Copy no. per cell 30° C. | Copy no. per cell 42° C. | Stable inheritance |
|---|---|---|---|---|---|---|
| pOU51 | Km,$\lambda$ | EcoRI | None | 25 | >1000 | Yes |
| pOU53 | $\lambda$ | EcoRI | None | 25 | >1000 | Yes |
| pOU56 | Ap,$\lambda$ | EcoRI, BamHI | None | 25 | >1000 | Yes |
| pOU57 | Ap,$\lambda$ | EcoRI, BamHI | None | 25 | >1000 | Yes |
| pOU71 | Ap,$\lambda$ | EcoRI, BamHI | None | 3 | >1000 | No |
| POU73 | Ap,$\lambda$ | BamHI | None | 1 | >1000 | No |
| pOU75 | Ap,$\lambda$ · | BamHI | None | 3 | >1000 | No |
| pOU106 | Ap,$\lambda$ | BamHI | None . | 3 | >1000 | No |
| pOU79 | Ap,$\lambda$,Lac(+) | EcoRI, BamHI | Lac−(EcoRI) | 3 | >1000 | No |
| pOU82 | Ap,$\lambda$,Lac+ | EcoRI, BamHI | None | 3 | >1000 | No |
| pOU91 | Ap,$\lambda$,Lac+, Par+ | EcoRI, BamHI | None | 3 | >1000 | Yes |
| pOU191 | Am, Cm, $\lambda$ | EcoRI | Cm$^s$ (EcoRI) | 3 | >1000 | No |
| pOU130 | Ap,$\lambda$,Lac+ | EcoRI | None | 3 | >1000 | Yes |
| pLC31 | Ap,RecA+ | EcoRI | RecA− | 3 | >1000 | No |
| pLC33 | Km,$\lambda$,Ap | EcoRI | None | 25 | >1000 | Yes |
| pLC34 | Km,$\lambda$ | EcoRI | None | 25 | >1000 | Yes |
| pOU110 | Ap | EcoRI, BamHI | None | a | | No |

$^a$copy number not temperature-dependent

BIBLIOGRAPHY

1. Published European Patent Application No. 78101877.5
2. Molin et al., J. Bact. 138, 1979, pp. 70-79.
3. Molin et al., Microbiology, 1981, pp. 408-411.
4. Rosen et al., Mol. Gen. Genet. 179, 1980, pp. 527-537.
5. Light and Molin, Mol. Gen. Genet. 184, 1981, pp. 56-61.

6. Stougaard et al., Proc. Natl. Acad. Sci. USA 78, 1981, pp. 6008–6012.
7. Molin et al., Mol. Gen. Genet. 181, 1981, pp. 123–130.
8. Stougaard et al., the EMBO Journal 1, 1982, pp. 323–328.
9. Sussman and Jacob, Compt. Rend. Acad. Sci. 254, 1962, p. 1517.
10. Sninsky et al., Gene 16, 1981, p. 275.
Uhlin et al., Gene 6, 1979, pp. 91–106.
12. J. Miller: *Experiments in Molecular Genetics*, Cold Spring Harbor Laboratory, Cold Spring Harbor, N.Y., 1972.
13. Davis, Botstein and Roth: *A Manual for Genetic Engineering; Advanced Bacterial Genetics*, Cold Spring Harbor, N.Y., 1980.
14. Bertani, J. Bact. 62, 1954, p. 293.
15. Bolivar et al., Gene 2, 1977, p. 95.
16. An & Friesen, J. Bact. 140, 1979, pp. 400–407.
17. Casadaban et al., J. Bact. 143, 1980, p. 971.
18. Dempsey & Willetts, J. Bact. 126, 1976, p. 166.
19. Nordström, Molin, Aagaard-Hansen, Plasmid 4, 1980, pp. 215–217.
20. Stougaard & Molin, Anal. Biochem. 118, 1981, p. 191.
21. Nordström et al., Plasmid 4, 1980, p. 322.
22. Valentin-Hansen et al., the EMBO Journal 1, 1982, p. 317.
23. Messing et al., Nucleic Acids Res. 9, 1981, p. 309.
24. Uhlin & Clark, J. Bact. 148, 1981, pp. 386–390.

We claim:

1. A plasmid requiring transcription from a promoter for replication, and which carries an inserted regulatable promoter at a position and in an orientation so that transcription from the promoter regulates plasmid replication, increased transcription from the promoter leading to a substantial increased or uncontrolled plasmid copy number.

2. The plasmid of claim 1, said plasmid capable of replicating in *Escherichia coli*.

3. A plasmid according to claim 1, in which the promoter is controllable by means of a regulating factor.

4. A plasmid according to claim 3, in which the regulating factor positively induces the promoter to increase transcription and plasmid replcation.

5. A plasmid according to claim 3, in which the regulating factor derepresses the promoter to increase transcription and plasmid replication.

6. A plasmid according to claim 1, in which the promoter is one which is chemically regulatable.

7. A plasmid according to claim 6, in which the promoter is a lac promoter, trp promoter or deo promoter.

8. A plasmid according to claim 1, in which the activity of the promoter is temperature-dependent.

9. A plasmid according to claim 1, in which the activity of the promoter is controlled by a temperature-sensitive regulating factor.

10. A plasmid according to claim 9, in which the promoter is a λ promoter, and in which the gene for a temperature-sensitive λcI repressor controlling transcription from said promoter is also present.

11. A plasmid according to claim 10, in which the promoter is either $\lambda P_R$ or $\lambda P_L$.

12. A plasmid according to claim 11, in which the promoter is $\lambda P_R$.

13. A plasmid according to claim 1, in which transcription from said regulatable promoter causes the plasmid to show a constant, low copy number at low temperatures and a substantially increased or uncontrolled copy number at higher temperatures.

14. A plasmid according to claim 13, in which transcription from said regulatable promoter causes the plasmid to show a constant, low copy number at a temperature of about 30° C. and a substantially increased copy number at a temperature in the range of about 36°–42° C.

15. A plasmid according to claim 14 showing an uncontrolled plasmid copy number at temperatures above about 39° C.

16. A plasmid according to claim 1, from which part of one native replication regulatory gene has been deleted and replaced by the regulatable promoter.

17. A plasmid according to claim 16 which, when host microorganisms containing the plasmid are grown under conditions securing a constant, low plasid copy number, has a copy number in the range of 20–40, and which, when the host microorganisms are grown under different conditions leading to a substantially increased or uncontrolled plasmid copy number, has a copy number in the range of at least about 500–1000 copies per cell.

18. A plasmid according to claim 17, wherein the plasmid has a copy number in the range of 20–40 at one temperature and an increased or uncontrolled copy number in the range of at least 500–1000 copies per cell at a higher temperature.

19. A plasmic according to claim 18, wherein the plasmid has a copy number in the range of 20–40 at a temperature of about 30° C., and an increased or uncontrolled copy number in the range of at least about 500–1000 copies per cell at a temperature of about 42° C.

20. A plasmid accordingto claim 15 which is an R1-type plasmid from which the copB gene has been deleted and replaced by the regulatable promoter.

21. A plasmid according to claim 1, in which a regulatable promoter has been inserted upstream of the native replication control gene(s) of the plasmid.

22. A plasmid according to claim 21 which, when host microorganisms containing the plasmid are grown under conditions securing a constant, low plasmid copy number, has a copy number in the range of 3–5 copies per cell, and which when the host microorganisms are grown under different conditions leading to a substantially increased or uncontrolled plasmid copy number, has a copy number in the range of at least about 500–1000 copies per cell.

23. A plasmid according to claim 22, wherein the plasmid has a copy number in the range of 3–5 at one temperature and an increased or uncontrolled copy number in the range of at least about 500–1000 copies per cell at a higher temperature.

24. A plasmid according to claim 23, wherein the plasmid has a copy number in the range of 3–5 at a temperature of about 30° C., and an increased or uncontrolled copy number in the range of at least about 500–1000 copies per cell at a temperature of about 42° C.

25. A plasmid according to claim 23, which is an R1-type plasmid in which the regulatable promoter has been inserted upstream of the copB and copA genes.

26. A plasmic according to claim 1, wherein a regulatable promoter has been inserted in the replication region from which part of one native replication regulatory gene has been deleted, and in which the native replication regulatory gene has been inserted in a region of said plasmid where it is not naturally located.

27. A plasmid according to claim 26, which, when host micoorganisms are grown under conditions securing a constant, low plasmid copy number, has a copy number in a range of about 0.5–1 copy per cell, and which when the host micoorganisms are grown under different conditions leading to a substantially increased or uncontrolled plasmid copy number, has a copy number in the range of at least about 500–1000 copies per cell.

28. A plasmid according to cliam 27, wherein the plasmid has a copy number int he range of 0.5–1 at one temperature, and an increased or uncontrolled copy numberin the range of at least about 500–1000 copies per cell at a higher temperature.

29. A plasmid according to to claim 28, wherein the plasmid has a copy number in the range of 0.5–1 at a temperature of about 30° C., and an increased or uncontrolled copy number in the range of at least about 500–1000 copies per cell at a temperature of about 42° C.

30. A plasmid according to claim 26, comprising an R1-type plasmid in which the copB gene has been inserted at the EcoRI site outside the replication region of the plasmid.

31. A plasmid according to claim 1, which in addition to the first regulatable promoter regulating transcription of the replication region, carries a second inserted promoter controlling the expression of a structural gene inserted in the plasmid.

32. A plasmid according to claim 31, in which the second promoter regulating the expression of said gene is controllable.

33. A plasmid according to claim 31, in which said second inserted promoter controlling the expression of the structural gene is the $\lambda P_L$ promoter.

34. A plasmid according to claim 31 having a constant, low plasmid copy number and very little or no gene expression at one temperature and having a substantially increased or uncontrolled plasmid copy number and gene expression at a higher temperature.

35. A plasmid according to claim 34, having a constant, low plasmid copy number and very little or no gene expression at about 30° C., and having a substantially increased or uncontrolled plasmid copy number and gene expression at a temperature in the range of about 36°–42° C.

36. A plasmid according to claim 35 having an uncontrolled plasmid copy number and a very high gene expression at temperatures above 39° C.

37. A plasmid according to claim 1 which carries a marker useful for the selection of cells containing the plasmid.

38. A plasmid according to claim 37, in which the marker is a gene mediating antibiotic resistance to the host microorganism.

39. A plasmid according to claim 1 which additionally carries a gene or genes not naturally related to the plasmid.

40. A microorganism in which a plasmid according to claim 1 has been inserted.

41. A micoorganism according to claim 40 which is a bacterium.

42. A microorganism according to claim 41 which is a gram-negative and mesophilic bacterium.

43. A micoorganism according to claim 42 which is an *Escherichia coli*.

44. A method of constructing the plasmid of claim 1, comprising:
(a) inserting a regulatable promoter into a plasmid at a position where transcription from said promoter regulates plasmid replication, and
(b) identifying the plasmid so treated by screening for those plasmids whcih show a substantially increased or uncontrolled plasmid copy number under conditions wherein transcription from said promoter is increased.

45. A method according to claim 44, comprising:
(a) deleting part of one native replication regulatory gene, and
(b) inserting a DNA fragment including the regulatable promoter at the site of the partially deleted native replication regulatory gene.

46. A method according to claim 45, comprising:
(a) deleting the copB gene from the plasmid by cleaving with the restriction endonuclease Bgl11, and
(b) inserting a Bgl11 fragment including the regulated promoter at this site.

47. A method according to claim 44 comprising inserting the regulatable promoter into the plasmid upstream the native replication control gene(s).

48. A method according to claim 47 comprising inserting the regulatable promoter at the BglII site upstream of copB and copA genes.

49. A method according to claim 45, further comprisig reinserting the native replication regulatory gene at its original site in the plasmid to construct a plasmid in whic all native replication control genes are present.

50. A method according to claim 46, further comprising reinserting the copB gene at the Bgl11 site in the plasmid to construct a plasmid in which both the copB and the copA genes are present.

51. A method according to claim 45, further comprising inserting one native replication regulatory gene in a region of the plasmid where it is not naturally located.

52. A method according to claim 46, further comprisng inserting the copB gene at the EcoRI site outside the replication region of the plasmid.

53. A method of constructing the plasmid of claim 31, comprising (a) inserting a regulatable promoter into a plasmid at a position where transcription from said promoter regulates plasmic replication, and (b) inserting a second promoter at an appropriate restriction site in the plasmid, thereby permitting the insertion of a strucutural gene the expression of which is regulatable from said second promoter.

54. A method of producing a gene product of said plasmid DNA comprising:
cultivating host micoorganisms carrying a plasmid according to claim 71 for at least a period of cultivation under conditions securing increased transcription from said regulatable promoter, resulting in a substantially increased or uncontrolled plasmid copy number, and
harvesting, from the microbial culture, a gene product of the plasmid.

55. A method according to claim 54, comprising cultivating said host micoorganisms under conditions resulting in a constant, low plasmid copy number during the seeding and multiplication stages, until the desired number of cells has been obtained, and thereafter cultivating said host microorganisms under conditions leading to a substantially increased or uncontrolled plasmid copy number.

56. A method according to claim 54, comprising cultivating said host microorganisms under conditions where transcription from the promoter does not significantly influence the copy number of the plasmid, and thereafter adding a substance which induces promoter activity to the culture medium in an amount leading to a substantially increased or uncontrolled copy number.

57. A method according to claim 56, comprising maintaining conditions leading to a substantially increased or uncontrolled plasmid copy number for a period of time sufficient to obtain a substantial amplification of the plasmid, but sufficiently brief to avoid any substantial impairment of the microbial culture, and thereafter removing the substance inducing promoter activity from the culture medium resulting in a slow decrease in plasmid copy number to the pre-induction level.

58. A method according to claim 54, comprising cultivating said host microorganisms in the presence of a substance substantially inhibiting promoter activity, and thereafter reducing the concentration of said substance, resulting in activation of the promoter and a substantially increased or uncontrolled plasmid copy number.

59. A method according to claim 58, comprising maintaining the conditions leading to a substantially increased or uncontrolled copy number for a period sufficient to obtain a substantial amplification of the plasmid, but sufficiently brief to avoid any substantial impairment of the microbial culture, and thereafter adding the substance inhibiting promoter activity in an amount leading to a slow decrease in plasmid copy number to pre-induction level.

60. A method according to claim 54, wherein the cultivation conditions for securing increased transcription from the promoter comprise a temperature at or near which the plasmid copy number is substantially increased or uncontrolled.

61. A method according to claim 60, wherein said temperature is maintained until the growth of the host microorganism is inhibited by the formation of plasmid DNA or gene products from the plasmid.

62. A method according to claim 61, wherein said temperature is thereafter shifted to a temperature securing a low, constant plasmid copy number causing a slow decrease in the copy number of the plasmid until it reaches the initial level.

63. A method according to claim 62, wherein the temperature at which the plasmid has a constant, low copy number is a temperature of about 30° C., and the temperature at which the plasmid has a substantially increased or uncontrolled copy number is in the range of about 36°–42° C.

64. A method of preparing a plasmid according to claim 37, comprising inserting in said plasmid a DNA fagment carrying a marker useful for the selection of cells containing the plasmid.

65. A method according to claim 64, in which the marker is a gene mediating antibiotic resistance to the host micoorganism.

* * * * *

UNITED STATES PATENT AND TRADEMARK OFFICE
CERTIFICATE OF CORRECTION

PATENT NO. : 4,806,471

DATED : February 21, 1989

INVENTOR(S) : SOREN MOLIN et al.

It is certified that error appears in the above-identified patent and that said Letters Patent is hereby corrected as shown below:

Column 3, Line 57: Change "cl" to --cI--.

Column 4, Line 63: Change "reguitable" to --regulatable--.

Column 6, Line 46: Change "side" to --site--.

Column 8, Line 16: Change "plasimids" to --plasmids--.

Column 8, Line 54-55: change "palsmid" to --plasmid--.

Column 9, Line 9: change "cl$_{857}$" to --cI$_{857}$--.

Column 9, Line 18: change "HindlII" to --HindIII--. change "denoes" to --denotes--.

Column 9, Line 22: change "insert" to --inserted--.

Column 10, Line 44: After "resulting" insert --in--.

Column 12, Line 6: Change "cl" to --cI--.

Column 12, Line 9: Change "cl" to --cI--.

Column 12, Line 11: Change "cl$_{857}$" to --cI$_{857}$--.

Column 12, Line 51: Change "active" to --activate--.

Column 12, Line 57: Change "may reversed" to --may be reversed--.

Column 13, Line 6: Change "immedately" to --immediately--.

UNITED STATES PATENT AND TRADEMARK OFFICE
CERTIFICATE OF CORRECTION

PATENT NO. : 4,806,471

DATED : February 21, 1989

INVENTOR(S) : SOREN MOLIN et al.

It is certified that error appears in the above-identified patent and that said Letters Patent is hereby corrected as shown below:

Column 13, Line 34: Change "containg" to --containing--.

Column 14, Line 2: Change "trascribes" to --transcribes--.

Column 14, Line 34: Change "promoter-carring" to --promoter carrying--.

Column 15, Line 23: Change "espression" to --expression--.

Column 15, Line 32: Change "cI" to --cI--.

Column 18, Line 33: Change "standared" to --standard--.

Column 18, Line 54: Change "resstriction" to --restriction--.

Column 18, Line 61: Change "cI857" to --$cI_{857}$--.

Column 19, Line 63: Change "Plasmit" to --Plasmid--.

Column 20, Line 18: After "have" insert --been--.

Column 20, Line 27: Change "GbIII" to --BgIII--.

Column 20, Line 29: Change "CHS50" to --CSH50--.

Column 20, Line 42: Change "bacteriumn" to --bacterium--.

Column 20, Line 43: Change "jPL20" to --pJL20--.

Column 20, Line 49: Change "fromn" to --from--.

UNITED STATES PATENT AND TRADEMARK OFFICE
CERTIFICATE OF CORRECTION

PATENT NO. : 4,806,471

DATED : February 21, 1989

INVENTOR(S) : SOREN MOLIN et al.

It is certified that error appears in the above-identified patent and that said Letters Patent is hereby corrected as shown below:

Column 21, Line 27: change "CHS50" to --CSH50--

Column 22, Line 7: Change "predsence" to --presence--.

Column 22, Line 32: Change "palsmid" to --plasmid--.

Column 22, Line 33: change "pOUL57" to --pOU57--.

Column 25, Line 29: Change "uniqaue" to --unique--.

Column 26, Line 9: Change "repA+" to --repA$^+$--.

Column 26, Line 26: Change "uner" to --under--.

Column 26, Line 41: Change "manenr" to --manner--.

Column 26, Line 45: Change "generastions" to --generations--.

Column 27, Line 2: Change "on" to --in--.

Column 27, Line 14: Change "transferae" to --transferase--.

Column 27, Line 22-23: Change "restrictio" to --restriction--.

Column 27, Line 26: Change "inserton" to --insertion--.

Column 27, Line 37: Change "shownin" to --shown in--.

Column 27, Line 46: Change "wit" to --with--.

Column 27, Line 52: Change "adn" to --and--.

UNITED STATES PATENT AND TRADEMARK OFFICE
CERTIFICATE OF CORRECTION

PATENT NO. : 4,806,471

Page 4 of 6

DATED : February 21, 1989

INVENTOR(S) : SOREN MOLIN et al.

It is certified that error appears in the above-identified patent and that said Letters Patent is hereby corrected as shown below:

Column 27, Line 53: Change "cl" to --cI--.

Column 27, Line 62: Change "had" to --has--.

Column 28, Line 12: Change "plasmic" to --plasmid--.

Column 28, Line 54: Change "CHSD50" to --CSH50--.

Column 28, Line 58: Change "pIC31" to --pLC31--.

Column 29, Line 23: Change "HindlII" to --HindIII--.

Column 29, Line 28: Change "BanHI" to --BamHI--.

Column 29, Line 31: Change "Molecule" to --Molecular--.

Column 29, Line 67: After "same" insert --replication--.

Column 30, Line 1: Change "thsi" to --this--. Change "snownin" to --shown in--.

Column 30, Line 3: Change "Accesson" to --Accession--.

Column 30, Line 14: Change "pL32'" to --pLC32'--.

Column 30, Line 25: Change "folowing genotyupe" to --following genotype--.

Column 30, Line 27: Change "wit" to --with--.

Column 30, Line 32: Change "replcation" to --replication--.

UNITED STATES PATENT AND TRADEMARK OFFICE
CERTIFICATE OF CORRECTION

PATENT NO. : 4,806,471

DATED : February 21, 1989

INVENTOR(S) : SOREN MOLIN et al.

It is certified that error appears in the above-identified patent and that said Letters Patent is hereby corrected as shown below:

Column 31, Line 9: Change "Uhlin" to --11. Uhlin--.

Column 32, Line 17: change "plasid" to --plasmid--.

Column 32, Line 35: change "accordingto" to --according to--.

Column 33, Line 12: change "cliam" to --claim--.

Column 33, Line 13: change "int he" to --in the--.

Column 33, Line 15: change "numberin" to --number in--.

Column 34, Line 7: change "wncih" to --which--.

Column 34, Line 45: change "plasmic" to --plasmid--.

Column 36, Line 28: change "fagment" to --fragment--.

In FIG. 2: Change Letter "A" to --I--

In FIG. 2: Change Letter "B" to --II--

In FIG. 2: Change Letter "C" to --III--

In FIG. 2: Change Letter "D" to --IV--

In FIG. 2: Change Letter "E" to --V--

In FIG. 2: Change Letter "F" to --VI--

In FIG. 2: Change Letter "G" to --VII--

UNITED STATES PATENT AND TRADEMARK OFFICE
CERTIFICATE OF CORRECTION

PATENT NO. : 4,806,471

DATED : February 21, 1989

INVENTOR(S) : SOREN MOLIN et al.

It is certified that error appears in the above-identified patent and that said Letters Patent is hereby corrected as shown below:

In FIG. 2: Change Letter "H" to --VIII--

In FIG. 2: Change Letter "I" to --IX--

In FIG. 2: Change Letter "J" to --X--

Signed and Sealed this

Seventeenth Day of December, 1991

Attest:

*Attesting Officer*

HARRY F. MANBECK, JR.

*Commissioner of Patents and Trademarks*